(12) United States Patent
Leirs et al.

(10) Patent No.: US 12,343,458 B2
(45) Date of Patent: Jul. 1, 2025

(54) ALGORITHMS AND SYSTEMS FOR GENERATING PHOTON PATTERNS AND INDUCING RESPONSE IN ORGANISM

(71) Applicant: Explorentis, Heverlee (BE)

(72) Inventors: Olivier Leirs, Heverlee (BE); Yoeri Bertha Jozef Renders, Halen (BE); Vincent Jacobs, Heist-op-den-Berg (BE)

(73) Assignee: Explorentis, Heverlee (BE)

( * ) Notice: Subject to any disclaimer, the term of this patent is extended or adjusted under 35 U.S.C. 154(b) by 986 days.

(21) Appl. No.: 17/047,694

(22) PCT Filed: Apr. 18, 2019

(86) PCT No.: PCT/EP2019/060194
§ 371 (c)(1),
(2) Date: Oct. 15, 2020

(87) PCT Pub. No.: WO2019/202127
PCT Pub. Date: Oct. 24, 2019

(65) Prior Publication Data
US 2021/0162162 A1    Jun. 3, 2021

(30) Foreign Application Priority Data

Apr. 18, 2018  (EP) .................................... 18168020

(51) Int. Cl.
*A01K 45/00* (2006.01)
*A61L 2/00* (2006.01)
(Continued)

(52) U.S. Cl.
CPC ................ *A61L 9/18* (2013.01); *A01K 45/00* (2013.01); *A61L 2/0052* (2013.01); *A61M 21/00* (2013.01);
(Continued)

(58) Field of Classification Search
CPC ................................................ A61M 2250/00
See application file for complete search history.

(56) References Cited

U.S. PATENT DOCUMENTS 5,818,734 A     10/1998  Albright
2003/0009933 A1*  1/2003  Yoneda .................. A01G 7/045
                                                47/1.01 R
(Continued)

FOREIGN PATENT DOCUMENTS

KR           1887503 B1 *  8/2018  ............. G05B 23/02
WO      2015/154798 A1    10/2015
(Continued)

OTHER PUBLICATIONS

Database Medline [Online], US National Library of Medicine (NLM), Bethesda, MD, US; 2013, Schutkowski Alexandra et al: "UVB exposure of farm animals: study on a food-based strategy to bridge the gap between current vitamin D intakes and dietary targets.", XP002792189, Database accession No. NLM23894475 abstract & PLOS One 2013, vol. 8, No. 7, 2013, p. e69418, ISSN: 1932-6203.

*Primary Examiner* — Thaddeus B Cox
(74) *Attorney, Agent, or Firm* — N.V. Nederlandsch Octrooibureau

(57) ABSTRACT

Algorithm for controlling a photon pattern generated by means of a multicolour LED lighting system and inducing by means of said photon pattern a desired response in an organism, said algorithm being in a format executable by a control system of the multicolour LED lighting system and comprising instructions to cause said control system to operate LEDs of the multicolour LED lighting system to emit at least one predetermined varying photon pattern. The instructions define at least the following group of parameters for each varying photon pattern to be emitted: target location, intensity, duty cycle and wavelength band, and varia- (Continued)

tions of at least one of said parameters over time. The instructions are such that the resulting varying photon pattern generated by means of the multicolour LED lighting system induces said desired response in said organism as a result of the combination of said defined parameters and the defined variations thereof.

18 Claims, 12 Drawing Sheets

(51) Int. Cl.
    *A61L 9/18*    (2006.01)
    *A61M 21/00*   (2006.01)
    *A61N 5/06*    (2006.01)
    *H05B 45/10*   (2020.01)
    *H05B 47/105*  (2020.01)
    *H05B 47/155*  (2020.01)

(52) U.S. Cl.
    CPC ........... *H05B 45/10* (2020.01); *H05B 47/105* (2020.01); *H05B 47/155* (2020.01); *A61M 2021/0044* (2013.01); *A61M 2250/00* (2013.01); *A61N 5/0618* (2013.01); *A61N 2005/0663* (2013.01)

(56) References Cited

U.S. PATENT DOCUMENTS

| | | |
|---|---|---|
| 2011/0147617 A1 | 6/2011 | Shur et al. |
| 2014/0352813 A1* | 12/2014 | Tharaldson ........ G05B 19/0425 |
| | | 702/138 |
| 2016/0089548 A1* | 3/2016 | Kaas ..................... A61N 5/0613 |
| | | 607/94 |
| 2018/0110207 A1* | 4/2018 | Suntych ................. G02B 26/04 |
| 2018/0369604 A1* | 12/2018 | Gamelin .................. A61N 5/06 |

FOREIGN PATENT DOCUMENTS

| | | |
|---|---|---|
| WO | 2016/033350 A1 | 3/2016 |
| WO | 2016/051207 A2 | 4/2016 |
| WO | 2017/087077 A1 | 5/2017 |

\* cited by examiner

ALGORITHMS AND SYSTEMS FOR GENERATING PHOTON PATTERNS AND INDUCING RESPONSE IN ORGANISM

FIELD OF THE DISCLOSURE

The present disclosure relates to algorithms and systems for generating, by means of LEDs of a multicolour LED lighting system, photon patterns by which desired responses can be induced in living organisms.

BACKGROUND ART

From WO 2014/138262 A1, systems are known for enhancing growth, destruction or repair in an organism comprising at least one photon emitter in communication with a photon emission modulation controller; wherein the at least one photon emitter is configured to emit at least one first photon pulse, wherein the at least one first photon pulse has a duration, intensity, wavelength band and duty cycle; wherein the at least one photon emitter is configured to emit at least one additional photon pulse, wherein the at least one additional photon pulse has a duration, intensity, wavelength band and duty cycle, wherein the duration, intensity, wavelength band and duty cycle of the at least one additional photon pulse is different from the duration, intensity, wavelength band and duty cycle of the at least one first photon pulse, wherein the photon emission modulation controller controls the emission of photons from the photon emitter; and wherein the at least one first photon pulse and the at least one additional photon pulse induce a desired response in the organism. Further provided are methods for the optimization of organism growth, destruction or repair through the use of high frequency modulation of photons of individual color spectrums.

U.S. Pat. No. 9,560,837B1 discloses a system for inducing a desired response in a bird, the system comprising: at least one photon emitter; at least one photon emission modulation controller in communication with the at least one photon emitter; where the at least one photon emitter is configured to produce a photon signal to the bird, where the photon signal comprises two or more independent components, where the two or more independent components comprise: a first independent component comprising a repetitive first modulated photon pulse group, where the first modulated photon pulse group has one or more photon pulse ON durations between 0.01 microseconds and 5000 milliseconds with one or more intensities, has one or more photon pulse OFF durations between 0.1 microseconds and 24 hours, and a wavelength color; and a second independent component comprising a repetitive second modulated photon pulse group, where the second modulated photon pulse group has one or more photon pulse ON durations between 0.01 microseconds and 5000 milliseconds with one or more intensities, has one or more second photon pulse OFF durations between is between 0.1 microseconds and 24 hours, and a wavelength color; where the first independent component and the second independent component are produced within the signal simultaneously; where the second modulated photon pulse group is different from the first modulated photon pulse group; and emitting the signal toward the bird from the at least one photon emitter, where the combined effect of the first modulated photon pulse group and the second modulated photon pulse group of the signal produces a desired response from the bird.

It has been found that the high-frequency photon modulation systems for inducing a desired response known in the prior art suffer from one or more disadvantages. Such disadvantages may comprise the need to employ specialized (often expensive) equipment, the complexity of use and programming experienced by the end-user, undesired side-effects or responses arising from the use of high-frequency photon bursts such as stimulation of wrong metabolic pathways or induction of stress, increased wearing down of electronic components, problems upon scaling to commercial sized systems (e.g. dephasing of signals in large systems) etc.

SUMMARY OF THE DISCLOSURE

It is a first aim of the present disclosure to provide improved algorithms, and systems, for generating photon patterns which induce a desired response in an organism.

It is a second aim of the present disclosure to provide a user interface for easily generating such algorithms.

It is a third aim of the present disclosure to provide a cloud system for distributing such algorithms.

It is a fourth aim of the present disclosure to provide methods of inducing a desired response in an organism by means of a photon pattern.

The present disclosure provides, according to a first aspect, an algorithm for controlling a photon pattern generated by means of a multicolour LED lighting system and inducing by means of said photon pattern a desired response in an organism, said algorithm being in a format executable by a control system of the multicolour LED lighting system and comprising instructions to cause said control system to operate LEDs of the multicolour LED lighting system to emit at least one predetermined varying photon pattern. The instructions define at least the following group of parameters for each varying photon pattern to be emitted: target location, intensity, duty cycle and wavelength band, and variations of at least one of said parameters over time. The instructions are such that the resulting varying photon pattern generated by means of the multicolour LED lighting system induces said desired response in said organism as a result of the combination of said defined parameters and the defined variations thereof.

In embodiments of the algorithm, the instructions may further define target subgroups of LEDs within said multicolour LED lighting system for emission of said at least one predetermined varying photon pattern. The target subgroups may for example be defined to obtain the desired photon pattern at the desired target location in a facility, such as for example an animal facility. The target subgroups for a photon pattern may also vary over time, e.g. the amount of LEDs in a subgroup may vary over time.

In embodiments, the algorithm may comprise instructions for emitting a sequence of predetermined varying photon patterns and/or inducing a sequence of desired responses in one or more organisms. Examples are disclosed herein below.

In embodiments, the algorithm may be further provided with a fail-safe mechanism, said fail-safe mechanism, for example a sub-routine in the algorithm, being provided for detecting and preventing the execution of forbidden or undesirable instructions. For example, said forbidden instructions may comprise instructions which may have a negative effect on the first or further desired response or on the organism, or trigger an undesired response.

In embodiments, the algorithm may comprise instructions for adapting said at least one predetermined varying photon pattern in response to feedback signals received from a feedback mechanism. Examples of feedback mechanisms and responses thereto are disclosed herein below.

In embodiments, the algorithm may be in a human-readable format, such as for example TXT, XML or other. An advantage may be that such formats can constitute a universal format for e.g. programming and distributing algorithms of varying photon patterns according to the present disclosure, and which may be easily converted by light controllers into control signals adapted to the local light infrastructure. This may in turn lead to standardisation.

The present disclosure provides, in a second aspect, a multicolour LED lighting system comprising a plurality of LEDs and a control system, e.g. one controller or multiple controllers which may be communicatively linked to each other, for example in a master-slave configuration. The control system is configured for operating said LEDs, i.e. the available light infrastructure, and the control system being provided with at least one algorithm as disclosed herein.

In embodiments of the multicolour LED lighting system, the control system may comprise a mapping module for mapping said algorithm, which may be in a human-readable format, on the plurality of LEDs (e.g. LED lamps or LED lighting modules) that are present in said LED lighting system. This means that the mapping module for example compares the instructions with the available resources and converts the instructions to appropriate control signals to generate the predetermined variable photon patterns, or close approximations thereof, using the available resources.

In embodiments of the multicolour LED lighting system, the control system may comprise at least one input for receiving feedback signals from a feedback mechanism. The control system may be provided for evaluating said feedback signals and adapting its operation of the LEDs based on said evaluation. Examples of feedback mechanisms and responses thereto are disclosed herein below.

In embodiments, the control system may be further provided with a fail-safe mechanism, said fail-safe mechanism, for example a software module in a controller of the control system, being provided for preventing the execution of forbidden or undesirable instructions contained in the algorithm being executed. For example, said forbidden instructions may comprise instructions which may have a negative effect on the first or further desired response or on the organism, or trigger an undesired response.

The present disclosure provides, in another aspect, an animal facility comprising a multicolour LED lighting system as disclosed herein.

The present disclosure provides, in another aspect, a cloud system for distributing algorithms as disclosed herein, the system comprising a cloud backend with a database containing said algorithms.

The cloud system may further comprising an editor software, for example accessible via a web browser application, for programming algorithms as described herein, the editor software comprising software components for generating, on a computer interface, user-editable graphic representations of said parameters and said variations thereof over time. In other words, the editor software may be provided for enabling or facilitating programming of such algorithms or "light recipes" in a graphic way.

BRIEF DESCRIPTION OF THE DRAWINGS

The present disclosure will be discussed in more detail below, with reference to the attached drawings.

The application file contains one or more drawings executed in colour, submitted in the form of a "pre-conversion archive".

DESCRIPTION OF EMBODIMENTS

Figure 1:
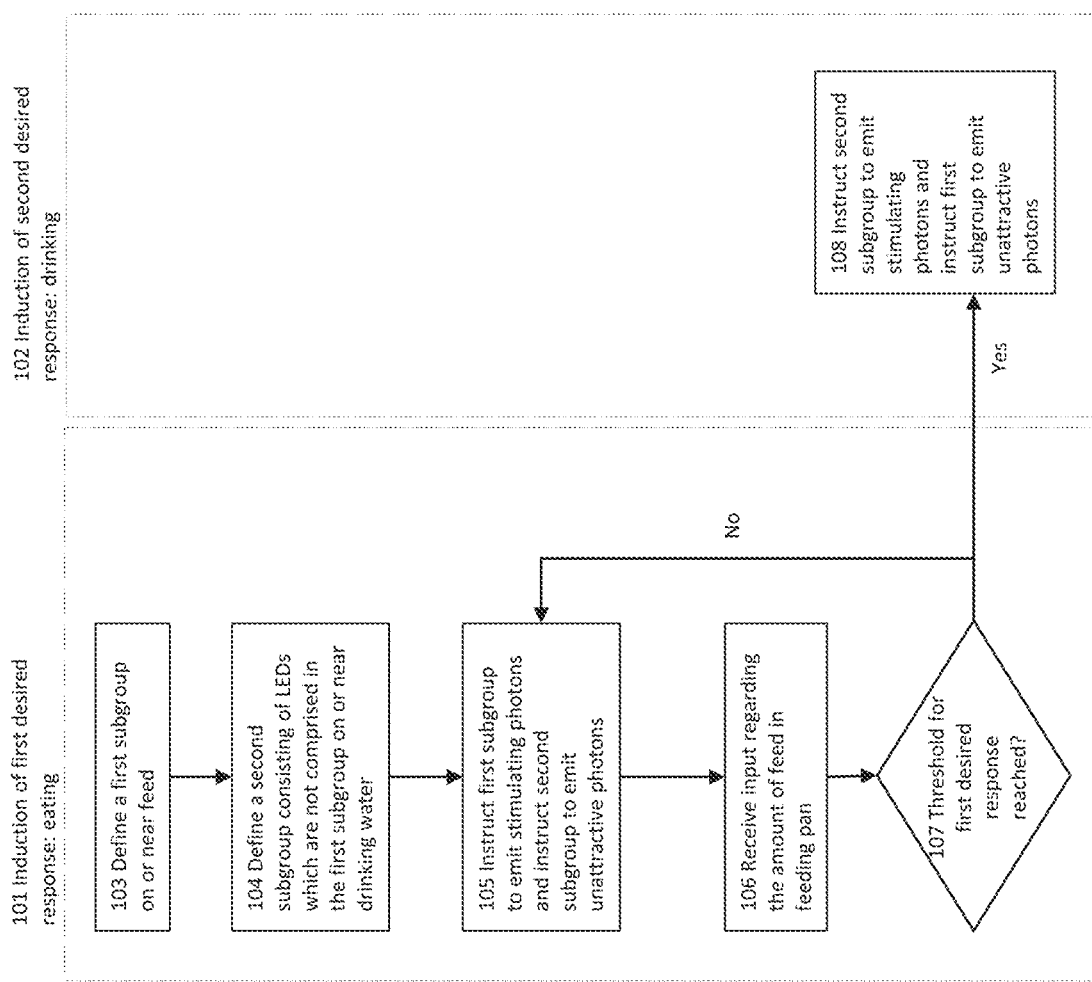
FIG. 1 shows a first example of an algorithm according to the present disclosure.

The present disclosure will be described with respect to particular embodiments and with reference to certain drawings but the disclosure is not limited thereto but only by the claims. The drawings described are only schematic and are non-limiting. In the drawings, the size of some of the elements may be exaggerated and not drawn on scale for illustrative purposes. The dimensions and the relative dimensions do not necessarily correspond to actual reductions to practice of the disclosure.

Furthermore, the terms first, second, third and the like in the description and in the claims, are used for distinguishing between similar elements and not necessarily for describing a sequential or chronological order. The terms are interchangeable under appropriate circumstances and the embodiments of the disclosure can operate in other sequences than described or illustrated herein.

Moreover, the terms top, bottom, over, under and the like in the description and the claims are used for descriptive purposes and not necessarily for describing relative positions. The terms so used are interchangeable under appropriate circumstances and the embodiments of the disclosure described herein can operate in other orientations than described or illustrated herein.

Furthermore, the various embodiments, although referred to as "preferred" are to be construed as exemplary manners in which the disclosure may be implemented rather than as limiting the scope of the disclosure.

The term "comprising", used in the claims, should not be interpreted as being restricted to the elements or steps listed thereafter; it does not exclude other elements or steps. It needs to be interpreted as specifying the presence of the stated features, integers, steps or components as referred to, but does not preclude the presence or addition of one or more other features, integers, steps or components, or groups thereof. Thus, the scope of the expression "a device comprising A and B" should not be limited to devices consisting only of components A and B, rather with respect to the present disclosure, the only enumerated components of the device are A and B, and further the claim should be interpreted as including equivalents of those components.

Introduction

Natural light is fundamentally different from the artificial light sources which are used today, for example in animal rearing or horticulture applications. Natural light is full spectrum, containing electromagnetic radiation at practically all wavelengths that are visible to the human eye (violet ~400 nm to red ~700 nm), and a range of wavelengths invisible to the human eye (infra-red and ultra violet). Natural light is dynamic, which means the intensity of the wavelengths observed at a fixed reference area (often depicted as a spectral power distribution) continuously change. Furthermore, the overall shape of the spectral power distribution changes with the time of day, time of year, the weather and the location on earth. For example, when the sun is overhead, daylight comprises relatively more blue light than during sunset, when it is dominated by orange and red. It is known that the dynamic nature of natural light is crucial in influencing organisms, for example by regulating circadian rhythms, hormone cycles, health, metabolism, behaviour etc.

The algorithms, systems, apparatuses and methods of the present disclosure provide varying photon patterns which can be customized, monitored and optimized for the specific and improved inducement of desired responses in target organisms, e.g. while better approaching natural light, which constantly varies in intensity and/or wavelength, which may result in maximizing the response and minimizing energy used in the system. By supplying control over the continuously changing parameters of a LED lighting system, which may include varying the groups of LEDs emitting the same pattern (LED subgroups), the present inventors have found that a wide variety of desired responses can be triggered in an alternative way, often in a gentle or low-stress manner for the organism. Other advantages may include a reduction in energy consumption and/or heat creation.

In an aspect, the present disclosure provides an algorithm for controlling the photon pattern emitted by means of a multicolour LED lighting system, and inducing by means of said photon pattern a first desired response in an organism; said LED lighting system may comprise at least two subgroups wherein each subgroup comprises one or more LEDs, said photon pattern resulting from the combination of photons emitted by each subgroup; said algorithm being in a format executable by a control system of the multicolour LED lighting system and comprising instructions to cause LEDs of the multicolour LED lighting system to emit photons; said instructions defining at least the following parameters: target subgroup of said LED lighting system and/or target location within a facility, intensity, duty cycle and wavelength band of the photon pattern, and the variation of said parameters over time, such that said instructions cause said photon pattern to vary over a predetermined time period and, wherein said varying photon pattern, or combinations of said varying photon patterns, induces said first desired response in the organism.

It should be noted that the 'instructions to cause LEDs of the multicolour LED lighting system to emit photons' as used herein refer to the instructions comprised in the algorithm, resulting in a LED output in accordance with the instructions. In practice, the instructions are generally translated into electric currents and/or control signals by means of a control system which are transmitted to the DIE. As the skilled person will understand, there may be a discrepancy between the instructions comprised in the algorithm and the electric currents transmitted to the DIE, for example if the instructions comprise instructions to execute a dimming effect of a LED (i.e. a decrease in intensity of a LED), the control system may transmit electric currents resulting in a change in the wavelength emitted by a DIE equipped with a phosphor filter, which in turn results in a LED dimming effect by means of the phosphor filter. In summary, the instructions of the algorithms as disclosed herein may be mapped onto the available light infrastructure, so as to obtain the desired varying photon patterns or at least close approximations thereof, to which end the control system may be equipped with a mapping module as described in an example below.

As used herein, the term "photon pattern" refers to the collection of photons emitted by groups of LEDs of the LED lighting system, which may be characterized by a distribution of wavelengths and an intensity, for example in the form of a spectral power distribution for every LED in the system, and their variation over time. The emitted spectrum may comprise not only visible light but also infra-red and ultra-violet light.

As used herein, "duty cycle" is the percentage of time electric current is delivered (and thus a LED is active) during the duration of one on/off cycle (the latter usually being 50 Hz).

As used herein "organism" includes an assembly of molecules functioning as a more or less stable whole that exhibits the properties of life. As will be discussed further, organisms may include but are not limited to unicells and multicellular life forms, viruses, animals (including but not limited to vertebrates (birds, mammals, amphibians, reptiles, fish); mollusks (clams, oysters, octopuses, squid, snails); arthropods (millipedes, centipedes, insects, spiders, scorpions, crabs, lobsters, shrimp); annelids (earthworms, leeches); sponges; and jellyfish, microorganisms, algae, bacteria, fungi, plants such as gymnosperms and angiosperms and pteridophytes, cyanobacteria or eukaryotic green algae. In preferred embodiments the organism does not comprise humans.

As used herein, "wavelength band" may refer to a narrow or broad range of wavelengths, which may also be characterized as a color, such as white, red, green, blue, yellow, cyan or as infrared, ultra-violet, including UV-A, UV-B, UV-C and combinations thereof. The skilled person will understand that, although LEDs are capable of emitting narrow wavelength bands, an instruction provided by the algorithm defining a wavelength band for a specific LED may result in that LED emitting wavelengths outside of that band, although most of the photons emitted by that LED will be within that band, for example 90% or more.

Preferred Organisms

Although the disclosure should not be construed as limited to a specific organism, in accordance with the disclosure, the organism is preferably a livestock animal, including avian species, aquatic species, and mammalian species. Examples of avian species include poultry species, such as turkey, duck and chicken. Examples of aquatic species include fish species, such as salmon, trout, tilapia, catfish and carp, and crustacean species, including shrimp and prawn. Examples of mammalian species include ruminant species, such as sheep, goat, and cattle, and non-ruminant species, such as horses, pigs and swine. In a preferred embodiment of the disclosure, the organism is selected from the group consisting of animals capable to perceive UV-A light. In other preferred embodiments the organism is selected from the group consisting of chickens, turkeys, ducks, quail, ostrich, pigs, horses, calves, goats, sheep, rabbits, dogs, cats and fish. In more preferred embodiments the organism is selected from the group consisting of chickens, turkeys, ducks, quail, ostrich, pigs, horses calves, goat sheep and rabbits, more preferably from the group consisting of chickens, turkeys, ducks, quail, ostrich, pigs, horses and calves, more preferably from the group consisting of chickens, turkeys, ducks, quail, ostrich and pigs, most preferably chickens, turkeys, ducks, quail, ostrich. In embodiments the organism is chicken.

In other embodiments the organism is selected from algae, bacteria, fungi, gymnosperms, angiosperms and pteridophytes, cyanobacteria or eukaryotic green algae. For example, the organism may be selected from *Arthrospira* spp., *Spirulina* spp., *Calothrix* spp., *Anabaena fibsaquae, Aphanizomenon* spp., *Anadaena* spp., *Gleotrichia* spp., *Oscillatoria* spp., *Nostoc* spp., *Synechococcus elongatus, Synechococcus* spp., *Synechosystis* spp. PCC 6803, *Synechosystis* spp., *Spirulina plantensis, Chaetoceros* spp., *Chiamydomonas reinhardii, Chiamydomonas* spp., *Chiorella vulgaris, Chiorella* spp., *Cyclotella* spp., *Didymosphenia* spp., *Dunaliella tertiolecta, Dunaliella* spp., *Botryococcus braunii, Botryococcus* spp., *Gelidium* spp., *Gracilaria* spp., *Hantscia* spp., *Hematococcus* spp., *Isochrysis* spp., *Laminaria* spp., *Navicula* spp., *Pleurochrysis* spp. and *Sargassum* spp; citrus, table grapes, wine grapes, bananas, papaya, *Cannabis* sp., coffee, goji berries, figs, avocados, guava, pineapple, raspberries, blueberries, olives, pistachios, pomegranate, artichokes and almonds; vegetables such as artichokes, asparagus, bean, beets, broccoli, brussel sprouts, chinese cabbage, head cabbage, mustard cabbage, cantaloupe, carrots, cauliflower, celery, chicory, collard greens, cucumbers, daikon, eggplant, endive, garlic, herbs, honey dew melons, kale, lettuce (head, leaf, romaine), mustard greens, okra, onions (dry & green), parsley, peas (sugar, snow, green, black-eyed, crowder, etc.), peppers (bell, chile), pimento, pumpkin, radish, rhubarb, spinach, squash, sweet corn, tomatoes, turnips, turnip greens, watercress, and watermelons; plants from the cannabis genus such as *Cannabis sativa, Cannabis indica*, or *Cannabis ruderalis*; flowering type bedding plants, including, but not limited to, *Ageratum, Alyssum, Begonia, Celosia, Coleus*, dusty miller, Fuchsia, Gazania, Geraniums, gerbera daisy, *Impatiens*, Marigold, *Nicotiana*, pansy/Viola, *Petunia, Portulaca, Salvia*, Snapdragon, *Verbena, Vinca*, and *Zinnia*; potted flowering plants including, but not limited to, African violet, Alstroemeria, Anthurium, Azalea, *Begonia*, Bromeliad, *Chrysanthemum, Cineraria*, Cyclamen, Daffodil/*Narcissus, Exacum, Gardenia, Gloxinia*, Hibiscus, Hyacinth, *Hydrangea*, Kalanchoe, Lily, Orchid, Poinsettia, *Primula*, regal pelargonium, rose, tulip, Zygocactus/Schlumbergera; foliage plants including, but not limited to, Aglaonema, Anthurium, Bromeliad, Opuntia, cacti and succulents, Croton, Dieffenbachia, Dracaena, Epipremnum, ferns, *ficus, Hedera* (Ivy), Maranta/Calathea, palms, Philodendron, *Schefflera*, Spathiphyllum, and *Syngonium*, cut flowers including, but not limited to, Alstroemeria, Anthurium, Aster, bird of paradise/*Strelitzia*, calla lily, carnation, *Chrysanthemum*, Daffodil/*Narcissus*, daisy, Delphinium, Freesia, *gerbera* daisy, ginger, *Gladiolus*, Godetia, *Gypsophila*, heather, iris, *Leptospermum*, Liatris, lily, *Limonium*, Lisianthus, Orchid, Protea, Rose, Statice, Stephanotis, Stock, Sunflower, Tulip; cut cultivated greens including, but not limited to, plumosus, tree fern, boxwood, soniferous greens, *Cordyline, Eucalyptus, hedera*/Ivy, holly, leatherleaf ferns, Liriope/Lilyturf, Myrtle, *Pittosporum*, Podocarpus; deciduous shade trees including, but not limited to, ash, birch, honey locust, linden, maple, oak, poplar, sweet gum, and willow; deciduous flowering trees including, but not limited to, *Amelanchier*, callery pea, crabapple, crapemyrtle, dogwood, flowering cherry, flowering plum, golden rain, hawthorn, *Magnolia*, and redbud; broadleaf evergreens including, but not limited to, Azalea, cotoneaster, *Euonymus*, holly, *Magnolia, Pieris*, Privet, *Rhododendron*, and *Viburnum*; coniferous evergreens including, but not limited to, Arborvitae, cedar, cypress, fir, hemlock, juniper, pine, spruce, yew; deciduous shrubs and other ornamentals including, but not limited to, buddleia, hibiscus, lilac, Spirea, *Viburnum*, Weigela, ground cover, *bougainvillea, clematis* and other climbing vines, and landscape palms; fruit and nut plants including, but not limited to, citrus and subtropical fruit trees, deciduous fruit and nut trees, grapevines, strawberry plants, other small fruit plants, other fruit and nut trees; cut fresh, strawberries, wildflowers, transplants for commercial production, and aquatic plants; pteridophyte plants including, but not limited to ferns and fungi including but not limited to basidiomycetes, ascomycetes, and sacchromycetes. Preferably the organism is selected from plants from the *Cannabis* genus such as *Cannabis sativa, Cannabis indica*, or *Cannabis ruderalis*.

Preferred Desired Responses

The algorithm in accordance with the disclosure may be used to induce a variety of desired responses in an organism, such as specific biochemical responses or behavioural responses, although the skilled person will understand that a behavioural response of an organism (such as an animal) may be a macroscopic effect of biochemical processes. Such responses may be related to the organism's growth, health, reproduction, cell metabolism, hormone metabolism, circadian cycle, behaviour etc. In preferred embodiments the desired response is a response relevant to the farming, horticulture, agriculture and/or animal rearing sectors.

Preferred desired responses for animals include influencing collective animal behaviour, in particular flocking behaviour in birds; influencing mood; reducing stress or anxiety levels; influencing reproductive behaviour, such as increasing reproductive behaviour or decreasing reproductive behaviour; influencing ovulation, such as stimulating ovulation or reducing ovulation; influencing egg laying behaviour, such as stimulating egg laying or discouraging egg laying; influencing feeding behaviour, such as increasing feed intake or reducing feed intake; improving feed conversion rate; reducing aggression; reducing feather picking; improving health; reducing pathogenic presence or infection such as bacterial, viral, parasitic, prions, fungal or algal presence or infection; increasing blood vitamin $D_3$ levels; improving Ca uptake; improving egg shell quality; improving bone stability; increasing egg vitamin $D_3$ levels; increasing meat vitamin $D_3$ levels; influencing the scurrying behaviour; and combinations thereof. Preferably the desired response is evaluated compared to a control group which is housed under similar conditions but employing conventional lighting.

The present inventors have found that the algorithm in accordance with the disclosure is specifically suitable for influencing many different aspects of collective animal behaviour. For example, as will be shown in the appending examples, for controlling where animals are located within their enclosures. The use of a varying photon pattern to induce such a response has many advantages as it may avoid or reduce stress, avoid or reduce physical harm (as may occur when animals are manually herded or driven into a section of their enclosure).

Preferred desired responses for plants include influencing fruit diameter such as increasing or decreasing the average fruit diameter; influencing stem diameter such as increasing or decreasing the average stem diameter; influencing leaf size such as increasing or decreasing the average leaf size; influencing leaf shape; influencing leaf temperature such as increasing or decreasing the average leaf temperature; activating flowering; influencing fruit ripening such as speeding up or slowing down fruit ripening; preventing pathogenic presence or infection such as viral, bacterial, fungal or parasitic presence or infection; influencing root growth such as increasing or decreasing total root surface; and combinations thereof. Preferably the desired response is evaluated compared to a control group which is grown under similar conditions but employing conventional lighting.

As used herein, 'inducing a desired response' should be construed as at least partially changing the state of an organism towards the desired response.

Plurality of Desired Responses

The algorithm in accordance with the disclosure may be provided to induce a first desired response in an organism, followed by a second desired response. Said second desired response may in turn be followed by a third desired response, etc. The algorithm in accordance with the disclosure may thus be provided to sequentially induce n desired responses in an organism, wherein n is an integer equal to or larger than 2.

In embodiments in accordance with the disclosure, there is thus provided an algorithm for controlling the photon pattern emitted by means of a multicolour LED lighting system, and induce by means of said photon pattern a first desired response followed by a second desired response in an organism; said LED lighting system may comprise at least two subgroups wherein each subgroup comprises one or more LEDs, said photon pattern resulting from the combination of photons emitted by each subgroup; said algorithm being in a format executable by a control system of the multicolour LED lighting system and comprising instructions to cause LEDs of the multicolour LED lighting system to emit photons, said instructions defining at least the following parameters: target subgroups of said LED lighting system and/or target location within a facility, intensity, duty cycle and wavelength band, and the variation of said parameters over time, such that said instructions cause said photon pattern to vary over a predetermined time period and, wherein said varying photon pattern induces said first desired response and said second desired response in the organism.

In embodiments in accordance with the disclosure, there is thus provided an algorithm for controlling the photon pattern emitted by means of a multicolour LED lighting system, and induce by means of said photon pattern a sequence of n desired responses in an organism, wherein n is an integer equal to or larger than 2; said LED lighting system may comprise at least two subgroups wherein each subgroup comprises one or more LEDs, said photon pattern resulting from the combination of photons emitted by each subgroup; said algorithm being in a format executable by a control system of the multicolour LED lighting system and comprising instructions to cause LEDs of the multicolour LED lighting system to emit photons, said instructions defining at least the following parameters: target subgroups of said LED lighting system and/or target location within a facility, intensity, duty cycle and wavelength band, and the variation of said parameters over time, such that said instructions cause said photon pattern to vary over a predetermined time period and, wherein said varying photon pattern induces said sequence of n desired responses in the organism.

The specific sequence of desired responses may be a cyclic sequence, such that when the $n^{th}$ desired response is induced, the algorithm reverts back to controlling the photon pattern to induce the first desired response etc.

An example of a cyclic sequence of desired responses is a sequence comprising the following responses:
wake up,
leave sleeping area,
reduce stress,
enter sleeping area, and
sleep
which is repeated every 24 hours.

Plurality of Target Organisms

The algorithm in accordance with the disclosure may be provided to induce a first desired response in a first organism, followed by a second desired response in a second organism.

In embodiments in accordance with the disclosure, there is thus provided an algorithm for controlling the photon pattern emitted by means of a multicolour LED lighting system, and induce by means of said photon pattern a first desired response in a first organism followed by a second desired response in a second organism; said LED lighting system may comprise at least two subgroups wherein each subgroup comprises one or more LEDs, said photon pattern resulting from the combination of photons emitted by each subgroup; said algorithm being in a format executable by a control system of the multicolour LED lighting system and comprising instructions to cause LEDs of the multicolour LED lighting system to emit photons, said instructions defining at least the following parameters: target subgroups of said LED lighting system and/or target location within the facility of the LED lighting system, intensity, duty cycle and wavelength band, and the variation of said parameters over time, such that said instructions cause said photon pattern to vary over a predetermined time period and, wherein said varying photon pattern induces said first desired response in said first organism and said second desired response in said second organism.

Variation Over Time

It was found that the simulation of natural light can be approached when the LEDs in the multicolour LED lighting system are not turned ON or OFF abruptly. Thus, in embodiments of algorithms according to the present disclosure, for at least 50%, at least 60%, at least 70%, at least 80%, at least 90%, at least 99% or all of the LEDs comprised in the LED lighting system, the variation of the intensity over time of a specific wavelength band emitted by a LED may be smaller than 50% of the intensity of the LED over a 1 µs, a 1 ms, a 1 s, a 10 s, a 100 s, a 1000 s or a 10000 s timeframe.

In embodiments of algorithms according to the present disclosure, at least 50%, at least 60%, at least 70%, at least 80%, at least 90%, at least 99% or all of the LEDs comprised in the LED lighting system are ON more than they are OFF, i.e. the duty-cycle is more than 0.5, within a 1 µs, a 1 ms, a 1 s, a 10 s, a 100 s, a 1000 s or a 10000 s timeframe.

In embodiments of algorithms according to the present disclosure, the photon pattern varies over a predetermined time period such that it is not repeated within a 1 µs, a 1 ms, a 1 s, a 10 s, a 100 s, a 1000 s or a 10000 s timeframe.

It was found that the algorithms in accordance with the disclosure may be used to provide a varying photon pattern which is optimized to induce a specific response, as explained herein and shown in the appending examples.

For example in a chicken farming facility, an algorithm in accordance with the disclosure is provided wherein the photon pattern varies such that within a timeframe of e.g. 30 minutes to 2 hours after an artificial or natural sunrise the photon pattern was dominated by blue light (i.e. the emitted wavelengths are predominantly corresponding to blue light), was found to have a beneficial effect on the egg laying behaviour, and specifically contributes to a reduction in the number of eggs which are laid on the ground. It is known that ground eggs are undesirable as they may be damaged, become dirty, carry infections, and the collection of ground eggs is a labour intensive process which stresses chickens.

In other embodiments there is provided an algorithm in accordance with the disclosure wherein the photon pattern varies such that alternating zones of relative shade are created. This has surprisingly been found to lead to an increase in movement of the animals and a reduction in the amount of leg-related injuries or problems. In embodiments an algorithm in accordance with the disclosure is provided wherein the photon pattern varies such, to create such zones of relative shade, that e.g. for at least 5 minutes, at least 30 minutes, at least 1 hour, at least 2 hours, at least 5 hours within a 24 hour timeframe, at least 10%, at least 20%, at least 30%, at least 50%, at least 70% or at least 80% of the LEDs comprised in the LED lighting system operate at an intensity below the average intensity calculated on the basis of all LEDs comprised in the LED lighting system, for example at an intensity of less than 90%, less than 80%, less than 70%, less than 50%, less than 30%, less than 20% of the average intensity. In embodiments an algorithm in accordance with the disclosure is provided wherein the photon pattern varies such, to create such zones of relative shade, that at least 10%, at least 20%, at least 30%, at least 50%, at least 70% or at least 80% of the LEDs comprised in the LED lighting system operate at an intensity of less than 60%, less than 50%, less than 40%, less than 30% or less than 20% of their maximum intensity. In embodiments, the LEDs may be divided up into subgroups, where the subgroup which operates at reduced intensity is varied over time, for example such that at one point in time a first subgroup operates at a reduced intensity and at a later point in time a second, different subgroup operates at a reduced intensity.

In embodiments, an algorithm in accordance with the disclosure is provided wherein said instructions are such that for at least 50%, at least 60%, at least 70%, at least 80%, at least 90%, at least 99% or all of the LEDs comprised in the LED lighting system, the change of intensity of a LED over time, is at least 10%, at least 20% or at least 30% of the maximum intensity of the LED, determined over less than 24 hours, less than 5 hours, less than 2 hours, less than 1 hour, less than 30 minutes, less than 5 minutes, less than 30 seconds, less than 1 second, less than 1 ms or less than 1 µs. In embodiments, the algorithm in accordance with the disclosure is provided wherein said instructions are such that for at least 50%, at least 60%, at least 70%, at least 80%, at least 90%, at least 99% or all of the LEDs comprised in the LED lighting system, the change of intensity of a LED over time, is lower than 90%, lower than 80% or lower than 70% of the maximum intensity of the LED, determined over at least 1 µs, at least 1 ms, at least 1 second, at least 30 seconds, at least 5 minutes, at least 30 minutes, at least 1 hour, at least 2 hours or at least 5 hours. It will be understood by the skilled person that high-frequency repetitive intensity changes or 'flickering' inherent to the light source, for example due to employing alternating current supply should not be taken into account and are generally not perceived by many organisms.

Multiple Subgroups

The present inventors have found that the algorithm in accordance with the disclosure can advantageously be used to control a plurality of LED subgroups wherein each subgroup comprises one or more LEDs, for example corresponding to predefined zones in a facility, e.g. a sleeping area, a feeding area, a drinking area, etc. It was found that when the different subgroups operate according to different instructions, inducement of specific responses can be optimized.

There is thus provided an algorithm in accordance with the disclosure, wherein the algorithm comprises the steps of:
defining a first subgroup,
defining a second subgroup comprising LEDs which are not comprised in the first subgroup,
and wherein the instructions for the first and second subgroup differ in at least one of the following parameters: intensity, duty cycle, wavelength band or the variation of said parameters over time. In a preferred embodiment at least 50%, at least 60%, at least 70%, at least 80%, at least 90%, at least 99% or all of the LEDs comprised in the second subgroup are not comprised in the first subgroup.

It was found that the use of an algorithm in accordance with the disclosure wherein at least one subgroup employs light which is agitating or unattractive to many animals, and at least one subgroup employs light which is stimulating or attractive to many animals, animal behaviour can be drastically influenced. There is thus provided an algorithm in accordance with the disclosure, wherein the algorithm comprises the steps of:
defining a first subgroup
defining a second subgroup comprising LEDs which are not comprised in the first subgroup,
wherein the instructions for the first and second subgroup differ in at least one of the following parameters: intensity, duty cycle, wavelength band or the variation of said parameters over time and wherein the first or the second subgroup emits stimulating or attractive photons and the other subgroup emits agitating or unattractive photons. Which photons are stimulating or attractive will depend on the specific animal. Similarly, which photons are agitating or unattractive will depend on the specific animal. For agitating or unattractive, light emitted in a flickering or stroboscopic manner, for example simulating lightning, may also be used. The choice of photon patterns for stimulating/attractive and agitating/unattractive may involve a user input upon setting up a lighting system, or applying a new algorithm thereto, in an animal facility. For example, the user may be requested, using set-up software on a computer device (temporarily) connected to the control system, to input information about the animals that will be housed in the facility, e.g. which animal, age, etc.

Figure 7B:
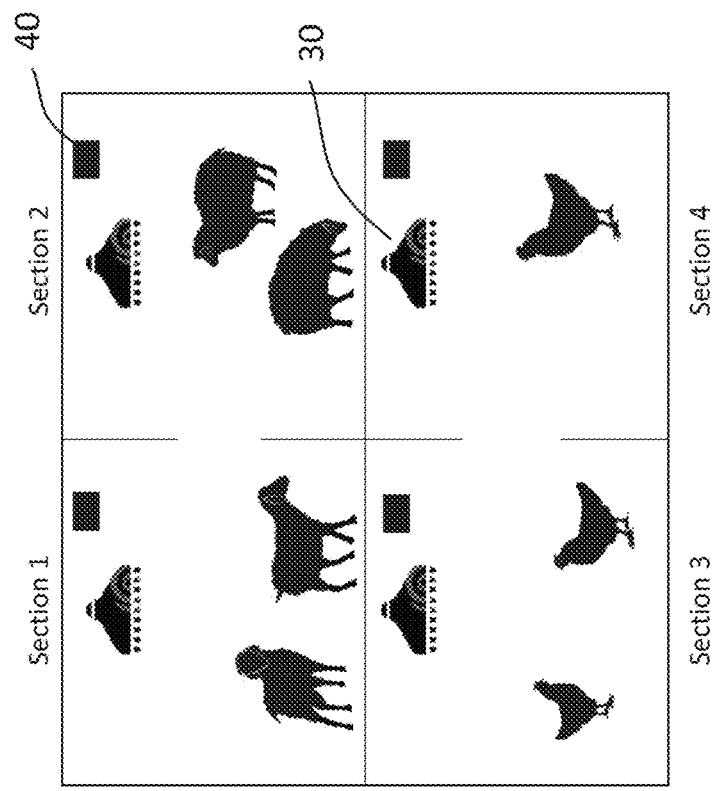
FIGS. 7a and 7b show schematic views of sections employed with LED multicolour lighting systems in accordance with the present disclosure.
Figure 7A:
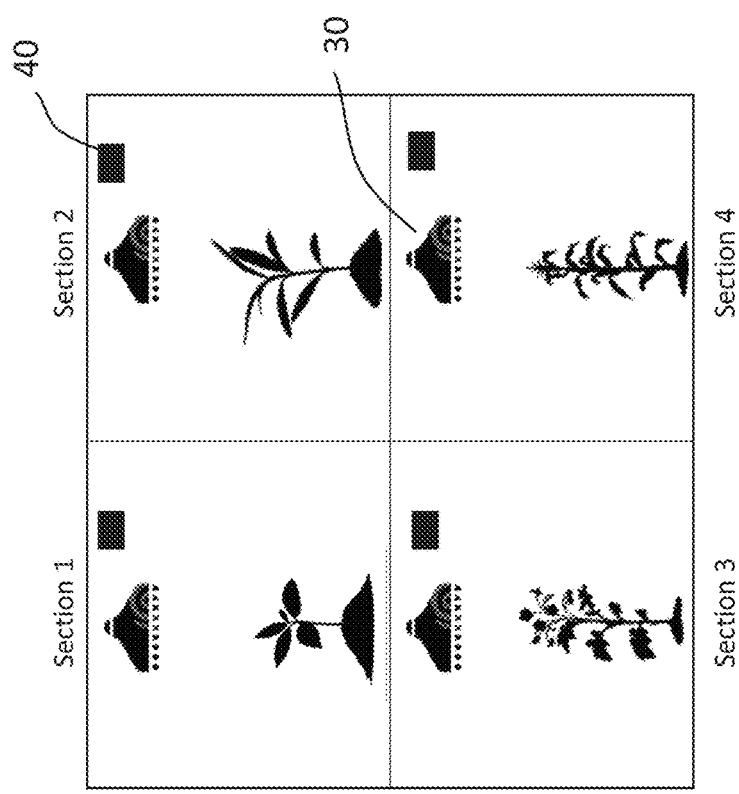

In an embodiment shown in FIG. 7a, the growing behaviour of plants, fruits and/or vegetables, may be influenced by an algorithm in accordance with the disclosure, wherein the algorithm comprises the steps of:
defining a first subgroup on or near growing plants
defining a second subgroup comprising LEDs which are not comprised in the first subgroup on or near blooming plants, fruits and/or vegetables,
wherein the instructions for the first and second subgroup differ in at least one of the following parameters: intensity, duty cycle, wavelength band or the variation of said parameters over time and wherein the first or the second subgroup emits stimulating or attractive photons and the other subgroup emits agitating or unattractive photons. In preferred embodiments the first or the second subgroup emits stimulating or attractive photons and the other subgroup simultaneously emits agitating or unattractive photons. For example, the stimulating or attractive (respectively, agitating or unattractive) photons may stimulate (respectively, agitate) growth of a plant or blooming of flowers, fruits and/or vegetables. In FIG. 7a, sections 1 and 2 show different stages of plant growth where the lighting system 30 comprises the first subgroup; section 3 shows blooming of a flower plant, and section 4 shows blooming of vegetable or fruit, where the lighting system 30 comprises the second subgroup.

An input system 40 comprising at least one sensor may supply sensor data to the lighting system 30 or other computing systems. In FIG. 7a, the sensor may be a camera supplying images of the plants in different sections and at different stages of the plants growth stages. In FIG. 7b, the sensor may be an ammonia sensor supplying data on ammonia levels in the sections to detect/monitor the concentration of feces. As will be described herein in more detail, other sensors ad combinations thereof are possible.

In an embodiment shown in FIG. 7b, feeding behaviour may be influenced by an algorithm in accordance with the disclosure, wherein the algorithm comprises the steps of:
  defining a first subgroup on or near feed,
  defining a second subgroup comprising LEDs which are not comprised in the first subgroup on or near drinking water,
wherein the instructions for the first and second subgroup differ in at least one of the following parameters: intensity, duty cycle, wavelength band or the variation of said parameters over time and wherein the first or the second subgroup emits stimulating or attractive photons and the other subgroup emits agitating or unattractive photons. In preferred embodiments the first or the second subgroup emits stimulating or attractive photons and the other subgroup simultaneously emits agitating or unattractive photons.

As described herein earlier, an algorithm may be provided for inducing several desired responses, for example a first desired response which is stimulating animals to eat, followed by a second desired response which is stimulating animals to drink. This algorithm has been found to result in an increased feed conversion rate and/or decreased time until slaughter weight is achieved.

In other embodiments, an algorithm in accordance with the disclosure is used to herd, drive or group animals into specific zones of the area covered by the LED lighting system. This may be useful in many situations, for example when a section of the animal pen or housing needs to be cleaned, or when animals need to be collected for slaughter etc. There is thus provided an algorithm in accordance with the disclosure, wherein the algorithm comprises the steps of:
  defining a first subgroup
  defining a second subgroup comprising LEDs which are not comprised in the first subgroup,
wherein the instructions for the first and second subgroup differ in at least one of the following parameters: intensity, duty cycle, wavelength band or the variation of said parameters over time, wherein the first or the second subgroup emits stimulating or attractive photons and the other subgroup simultaneously emits agitating or unattractive photons for more than 30 seconds, preferably more than 1 minutes, preferably more than 5 minutes.

It has been found that the algorithm in accordance with the disclosure may be used to prevent animals from pressing up against the enclosure of the cage, which is known to cause harm or suffocation. In embodiments, there is thus provided an algorithm in accordance with the disclosure, wherein the algorithm comprises the steps of:
  defining a first subgroup on or near the enclosure of an animal cage,
  defining a second subgroup comprising LEDs which are not comprised in the first subgroup,
wherein the instructions for the first and second subgroup differ in at least one of the following parameters: intensity, duty cycle, wavelength band or the variation of said parameters over time, wherein the first subgroup emits agitating or unattractive photons for more than 30 seconds, preferably more than 1 minutes, preferably more than 5 minutes.

Fail Safe Mechanism

In order to improve the safety and/or efficiency of the algorithm, the present inventors have found that it may be desirable to employ a fail-safe mechanism in the algorithm, or in the control system executing the algorithm. Thus, in embodiments there is provided a fail-safe mechanism, said fail-safe mechanism being provided for detecting and preventing the execution of forbidden or undesirable instructions. For example, said forbidden instructions comprises instructions which have a negative effect on the first or further desired response or on the organism, or trigger an undesired response. Such forbidden instructions may occur inadvertently as a result of a user programming an algorithm or "light recipe" as disclosed herein, e.g. combining multiple varying photon patterns in different zones or target location of a facility. As a result, there may be a need for a.o. detecting the occurrence of undesired combinations of photon patterns.

Response Feedback Mechanism

In order to improve the efficiency of the algorithm or respond to unforeseen situations, the present inventors have found that it may be desirable to employ a response feedback mechanism in the algorithm. Thus, in embodiments there is provided an algorithm in accordance with the disclosure, wherein the algorithm is further provided with a response feedback mechanism, said response feedback mechanism comprising the steps of:
  receiving input regarding the status of inducing the current desired response,
  optionally altering the sequence of photon patterns associated with desired responses,
  optionally defining new subgroups, and
  adapting or maintaining the instructions based on said input.

Suitable input regarding the status of inducing the current desired response may comprise data regarding flocking behaviour, stress, reproductive behaviour, egg laying behaviour, blood analysis results, excrement analysis results, feed behaviour, fruit diameter, stem diameter, leaf size, leaf shape, leaf temperature, natural light conditions, or other data, and combinations thereof. In embodiments the input regarding the status of inducing the current desired response comprises blood analysis results or excrement analysis results, comprising data on the concentration of luteinizing hormones.

In embodiments, the input may be data supplied by; or data generated by an algorithm based on data supplied by: a stem diameter sensor, a fruit diameter sensor, a leaf temperature sensor, a relative-rate sap sensor, an infrared sensor, a gas analysis sensor, a photorespiration sensor, a respiration sensor, a camera, a near-infrared sensor, a pH sensor, a sound recording device, a feed consumption monitoring device, water consumption monitoring device, other fluid consumption monitoring device, a spectral sensor located outside, user input and combinations thereof. In case the target organism is an animal, preferably the input comprises data supplied by a camera or sound recording device. Image or sound recognition software, known per se in the art, may be used to analyse the recorded images or sounds and generate feedback data from this analysis.

In preferred embodiments, the input comprises data supplied by; a gas analysis sensor, a pH sensor, a camera, a sound recording device (e.g., a microphone), a feed consumption monitoring device, a water consumption monitoring device (e.g. a flow sensor), or combinations thereof.

A preferred input comprises data supplied by a gas analysis sensor provided for sensing ammonia, in particular in the case of poultry, for example to detect high concentrations of feces.

Figure 8:
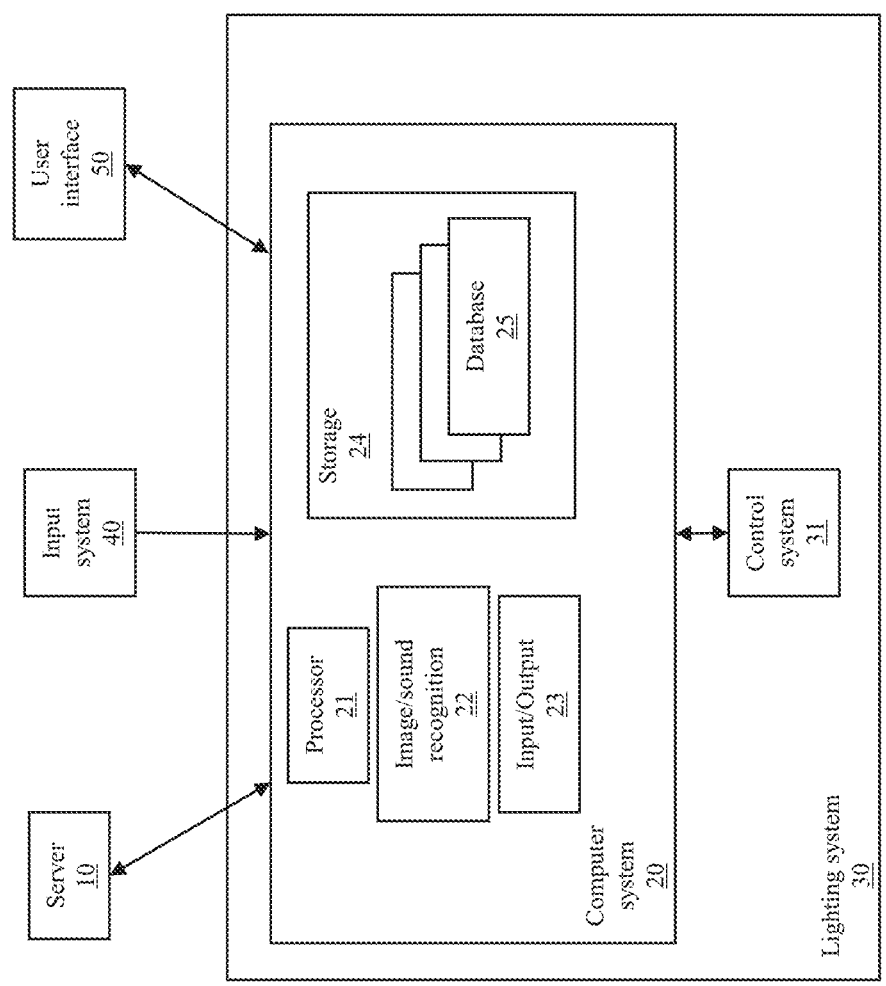
FIG. 8 shows a schematic diagram illustrating a lighting system according to the present disclosure.
Figure 9:
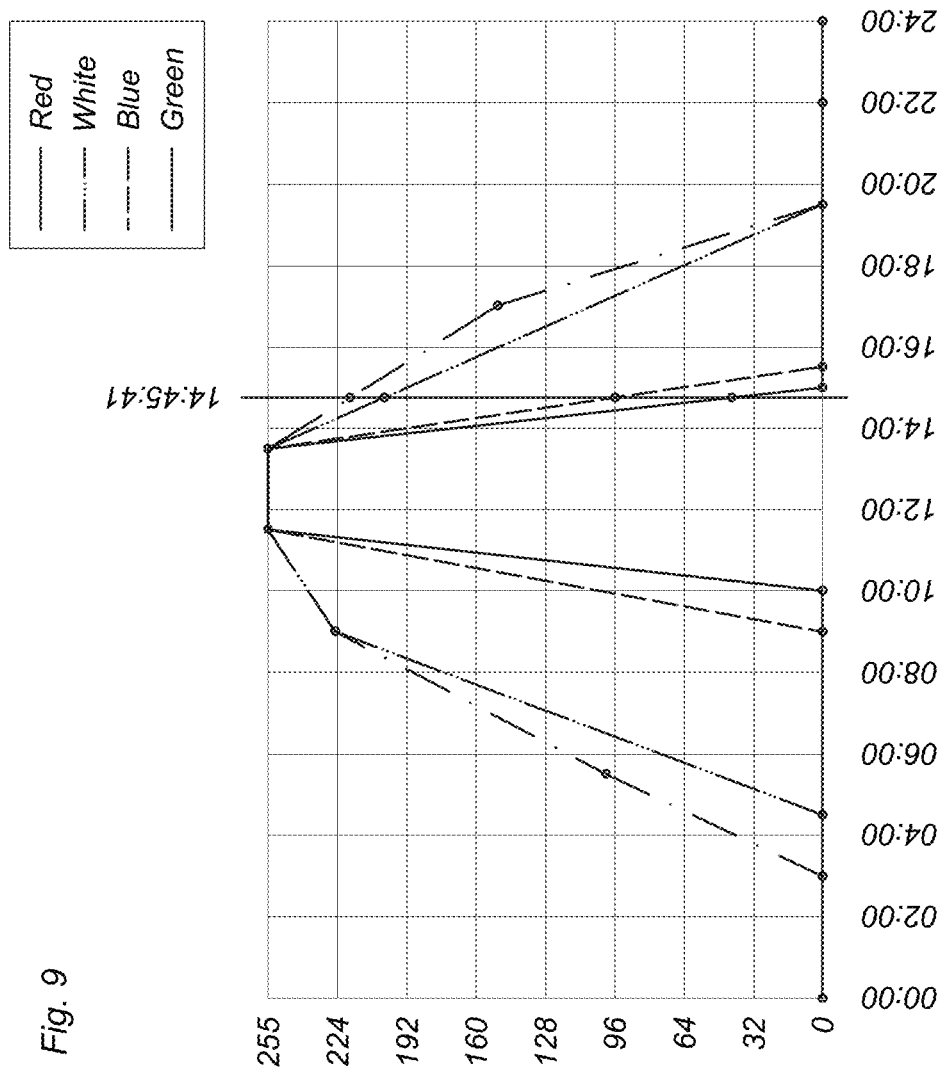
FIG. 9 shows a graphic representation of a varying or dynamic photon pattern, used in even another example according to the present disclosure.

In embodiments, the input may be data supplied by an input system 40 (FIG. 8) comprising a stem diameter sensor, a fruit diameter sensor, a leaf temperature sensor, a relative-rate sap sensor, an infrared sensor, a gas analysis sensor, a photorespiration sensor, a respiration sensor, a camera, a near-infrared sensor, a pH sensor, a sound recording device, a feed consumption monitoring device, a spectral sensor located outside, or combinations thereof. In case the target organism is an animal, preferably the input comprises data supplied by a camera, e.g. an infrared camera, and/or a sound recording device. Image or sound recognition software, known per se in the art, may be used to analyse the recorded images or sounds and generate feedback data from this analysis.

In embodiments, the input may be data generated by an algorithm based on data supplied by an input system 40 (FIG. 8) comprising a stem diameter sensor, a fruit diameter sensor, a leaf temperature sensor, a relative-rate sap sensor, an infrared sensor, a gas analysis sensor, a photorespiration sensor, a respiration sensor, a camera, a near-infrared sensor, a pH sensor, a sound recording device, a feed consumption monitoring device, a spectral sensor located outside, or combinations thereof. In case the target organism is an animal, preferably the input comprises data supplied by a camera, e.g. an infrared camera, and/or a sound recording device. Image or sound recognition software, known per se in the art, may be used to analyse the recorded images or sounds and generate feedback data from this analysis.

As is used herein, the term 'image' refers to one or more images which are taken by one or more cameras in the form of still or motion images (i.e. video). As described in detail later herein, images may be used in animal recognition for example to identify an individual animal among a plurality of specific animals or to identify a predefined pattern of one or more animals.

As explained above, it is advantageous that the photon pattern emitted by means of the multicolor LED lighting system goes at least some way towards simulating natural light. There is thus provided an algorithm in accordance with the disclosure, which takes into account data regarding natural light, for example the spectral power distribution and its variation over time, which may be recorded near the location where the multicolor LED lighting system is employed, or anywhere in the world, for example in the natural habitat of the animal or plant being reared. The data may be real-time or historical.

In embodiments, there is provided an algorithm in accordance with the disclosure, wherein the algorithm is further provided with a response feedback mechanism, said response feedback mechanism comprising the steps of:
receiving input regarding the status of inducing the current desired response, said input comprising data regarding real-time natural light conditions,
optionally altering the sequence of photon patterns associated with desired responses,
optionally defining new subgroups, and
adapting or maintaining the instructions based on said input.

The skilled person will understand that real-time data means data recently recorded, for example within one hour before being processed in the algorithm. In embodiments, the LED lighting system is located in a greenhouse and the algorithm provides instructions such that the photon pattern at least partially compensates for the light absorbed or reflected by the greenhouse glass.

As the algorithm in accordance with the disclosure may be employed in a large variety of contexts, the present inventors envisage the use of artificial intelligence and self-learning capabilities, for example in conjunction with the response feedback mechanism described herein. This allows the algorithm to improve the response to a specific input. In accordance with the invention, the self-learning capabilities may take form of a self-learning image recognition system, a self-learning sound recognition system, or a combination thereof. In this way, for example, various photon patterns or sequences thereof can be tested while using the self-learning capabilities of the response feedback mechanism to determine optimal photon patterns or sequences thereof for achieving the desired response(s).

Thus, in embodiments there is provided an algorithm for controlling a photon pattern generated by means of a multicolour LED lighting system in accordance with the disclosure, wherein the algorithm is further provided with a response feedback mechanism, said response feedback mechanism comprising the steps of:
receiving input regarding the status of inducing the current desired response,
optionally altering the sequence of photon patterns associated with the desired responses,
optionally defining new subgroups, and
adapting or maintaining the instructions based on said input,
and wherein said input regarding the status of inducing the current desired response is the output data received from a self-learning image recognition system, a self-learning sound recognition system, or a combination thereof.

As will be understood by the skilled person in light of the present disclosure, the input regarding the status of inducing the current desired response based on image and/or sound recognition is preferably provided by one or more image and/or sound recognition software applications. Thus, in preferred embodiments of the invention, such as in the embodiment shown in FIG. 8, the multicolour LED lighting system 30 comprises a computer system 20, said computer system 20 being provided with one or more image and/or sound recognition applications. The computer system 20 further comprises one or more processor units 21 provided for executing/operating the one or more image and/or sound recognition applications, and one or more optionally cloud-based storage units 24 provided for storing the one or more image and/or sound recognition applications. As described in more detail herein, the image and/or sound recognition system 22 utilizes one or more learned models for animal classification.

The one or more storage units 24 may comprise one or more databases 25. The computer system 20 may further comprises an input/output unit 23 configured for receiving input signals from the input system 40, and configured for transmitting output signals to a user interface 50 (e.g. a mobile device, a screen or other means of communicating with a user), the control system 31 of the multicolor LED lighting system 30, or to a storage unit (e.g., the one or more databases 25 or the server 10). Preferably, the input/output unit 23 is configured for transmitting output signals to the control system 31 of the multicolor LED lighting system 30. The input system 40 comprises an image recording means (such as a photocamera or a videocamera) and/or a sound recording means (such as a microphone). In an embodiment the input system 40 comprises 1 or more, such as 1-5 videocameras which are placed such that they can capture footage from an animal enclosure, such as a chicken coop. In embodiments the input system comprises more than 1 videocamera, wherein the videocameras are distributed over the animal enclosure, such as a chicken coop. For example, the input system may comprise at least one videocamera placed such that it can capture footage of the feeding and/or drinking area, and at least one videocamera placed such that it can capture footage of the resting area. In an embodiment, the input/output unit 23 of the computer system 20 may be further provided to output signals to a user through the user-interface 50 wherein the output data comprises status information of one or more animals, such as stress, disease, activity level, location, movement, etc. and/or instructions, for example to remove one or more specific animals, or to perform a certain activity in an empty area such as cleaning. Thus, the output data may be provided for effectively managing, for example, an animal facility.

In embodiments, the computer system 20 may store the input data along with the corresponding output data in the one or more databases 25.

In embodiments, the control system 31 and the computer system 20 may be the same system.

The one or more image and/or sound recognition applications 22 preferably leverages multiple cues and utilizes one or more learned models for classification. In embodiments of the invention the one or more image and/or sound recognition applications 22 utilize a classification scheme including unsupervised feature extraction and classification. Unsupervised feature extraction may be performed utilizing different methods known in the art. Unsupervised feature extraction is a lightweight feature extraction scheme that facilitates learning appearance descriptors based on one or more constraints (e.g., constraints of a control system, such as small training data size, memory/computational costs, etc.). In one embodiment, unsupervised feature extraction is performed utilizing Convolutional Sparse Coding (CSC) and manifold learning. Similar to using a deep neural network, unsupervised feature extraction produces highly diverse feature filters, allowing capture of both low and high level features. Further, unlike a complex learning framework that utilizes a deep neural network, unsupervised feature extraction significantly reduces model complexity and preserve hierarchical level features. Also, unsupervised feature extraction may utilize a single-layer feature extraction scheme instead of a multi-layer deep neural network to reduce computation time.

The one or more image and/or sound recognition applications 22 further comprises a classification unit. The classification unit is configured to classify a feature (such as the type of animal included in the input data) based on a learned classification model (e.g., a learned classification model trained by a training module). In one embodiment, the classification unit comprises at least one of the following: (1) a feature extraction unit configured to apply a single-layer feature extraction scheme that provides both low-level feature representation and high-level feature representation of the object, (2) a manifold learning unit configured to apply a learned projection matrix (e.g., a learned projection matrix trained by the training module) to reduce feature dimensions, and (3) a classifier configured to map a feature to a corresponding feature category based on the learned classification model. Preferred classification models allow the classification of an image and/or sound into one or more category comprising at least one of an individual (e.g. based on species, type of animal within a specific species, individual within a specific type of animal, etc.) an activity status (e.g. sleeping, eating, drinking, resting, moving, fighting, etc.), a health status (e.g. sickness level, stress level, size relative to age, infections, diseases, might or lice infestations, quality of fur, feathers or skin etc.), any other type of status relating to moods/atmospheres of animals or the like.

As stated above, the feature extraction unit of the one or more image and/or sound recognition applications 22 may be provided to utilize a single-layer feature extraction scheme that provides both low-level feature representation and high-level feature representation of an object. For example, instead of utilizing a multi-layer deep neural network, the single-layer feature extraction scheme may be implemented as a pipeline. In an embodiment concerning image recognition, before applying feature extraction, the trained images may be aligned, by means for aligning images known in the art, such as estimating a camera pose of an input image, etc., and resized into the same size (e.g. 100×100, 300×200, 120×240, etc.) or aspect ratio (e.g 1:1, 3:2, 4:3, 5:4, etc.). In embodiments, the pipeline may comprise the following three cascaded layers: (1) an element-wise absolute value rectification (ABS) layer, (2) a local contrast normalization (LCN) layer 231C, and (3) a max-pooling (MP) layer. These layers are applied in the described order, wherein the ABS layer is configured to compute an absolute value element-wise for a given feature map, the LCN layer is configured to apply local subtractive and divisive operations within each feature map to enhance stronger feature responses and suppresses weaker ones across the feature map, and the MP layer is configured to down-sample the feature maps and create position invariance over larger local regions. Max-pooling may be applied to select invariant features and improve generalization performance. One or more resulting feature maps are obtained after max-pooling.

In some embodiments, the pipeline may not include the ABS and LCN layers. Not having to perform ABS and LCN increases efficiency of the pipeline 235, thereby reducing overall computation time, especially for input data comprising a high-resolution image. As image recognition on images with abnormal lighting conditions becomes much more challenging without ABS and LCN, however, pre-processing steps may be incorporated at the beginning of the pipeline, such as an illumination and resolution detection layer. Multiple algorithms may be applied during these pre-processing steps, such as, but not limited to, measuring brightness of an input image as a reference of a condition of illumination.

In embodiments, the one or more image and/or sound recognition applications 22 further comprises a training module provided for training one or more learned models utilized by the image and/or sound recognition system 22 for classification. Examples of suitable training modules comprise feature databases, filter banks, classification models or projection matrices, etc.

In preferred embodiments, the training module comprises one or both of the following components: (i) a database builder configured for building one or more two-dimensional (2D) or three-dimensional (3D) feature databases for one or more animal classifications, and (ii) a feature learning unit configured for learning one or more 2D convolutional filter banks, a projection matrix for reducing feature dimensions, and a classification model.

In one embodiment, the training module may train offline one or more, such as all of the learned models utilized by the one or more image and/or sound recognition applications 22 for classification (i.e., not in the computer system comprised in the LED lighting system 30). For example, the training module trains the learned models on a remote server 10 utilizing computation resources of the server (e.g., one or more processors and/or one or more storage devices). Advantageously, training may be performed more efficiently. After training, the learned models may be loaded onto/downloaded to the computer system 20 or comprised in the one or more image and/or sound recognition applications 22. Advantageously, in case the connection to the remote server 10 is lost/broken due to software or hardware malfunctions, the computer system 20 can still function based on the last downloaded learning models. In another embodiment, training module may train the learned models in the computer system 20 itself.

In embodiments of the one or more image recognition applications 22 comprising a training module, the database builder (i) comprised in the training module may be configured to use one or more image databases for the one or more categories, as described above, wherein each image database corresponds to an category. For each category, the corresponding image database comprises a set of training images from the same category provided by the input system 40. In one embodiment, a set of training images includes a plurality of different 2D images capturing different illumination changes, different views, and different backgrounds of an animal. A category may represent a species, or more specifically, an animal in a specific species. In a preferred embodiment, the animal category is an individual animal in a group of animals of the same type. For example, a category may be an individual chicken in a flock of chicken. In embodiments of the training module, the database builder may be provided to build, for each animal category, a corresponding feature database. In an embodiment, the category may be an event involving one or more animals. For example, a pattern of one or more animals, such as a certain or no movement, cannibalism, one or more diseases, infestation of mites and/or lice, stress levels, etc., of one or more chickens in a flock of chicken.

In an alternative embodiments, the one or more image and/or sound recognition applications 22 may utilize a classification scheme including supervised learning. Thus, the images in the databases may be labelled by a user or a machine (e.g. an algorithm) on the previously described categories.

The feature learning unit (ii) comprised in the training module may be provided to apply Convolutional Sparse Coding, Convolutional Neural Networks or other methods known in the art to learn one or more 2D convolutional filter banks. Preferably, the feature learning unit (ii) is provided to apply a manifold learning algorithm to learn a projection matrix for reducing feature dimensions (i.e., original features to a low dimensional space). The manifold learning algorithm applied may be Orthogonal Locality Preserving Projections (OLPP) or another manifold learning scheme. In embodiments, the feature learning unit (ii) is provided to train a learned classification model for mapping a feature of a low-dimensional space to a corresponding animal category by training one or more support vector machines (SVMs) based on feature vectors. To prevent over-fitting, the feature learning unit (ii) may be provided wherein a validation set is randomly selected to optimize parameters for the SVMs, such that based on cross-validation, there are many different experimental folds, and a set of parameters with best performance is selected.

In an embodiment, the computer system 20 stores any of the transmitted data, i.e. signals, values, etc. in a storage unit (e.g., the one or more databases 25 or the server 10).

Internal Monitoring Feedback Mechanism

In order to improve the efficiency of the algorithm or increase the lifetime of the LED lighting system the present inventors have found that it may be desirable to employ an internal monitoring mechanism in the algorithm. Thus, in embodiments there is provided an algorithm in accordance with the disclosure, wherein the algorithm is further provided with an internal monitoring feedback mechanism, said internal monitoring mechanism comprising the steps of:

receiving input regarding the status of LED lighting system, optionally defining new subgroups, and adapting the instructions based on said input.

Ambient Conditions Feedback Mechanism

In order to improve the efficiency of the algorithm or respond to unforeseen situations, the present inventors have found that it may be desirable to employ an ambient conditions feedback mechanism in the algorithm. Thus, in embodiments there is provided an algorithm in accordance with the disclosure, wherein the algorithm is further provided with an ambient conditions feedback mechanism, said ambient conditions feedback mechanism comprising the steps of:

receiving input regarding the ambient conditions, optionally defining new subgroups, and adapting the instructions based on said input.

Suitable input regarding the ambient conditions may comprise data regarding the air or soil temperature, soil moisture levels, humidity levels, soil pH, etc., or input regarding other light sources in the vicinity of the LED lighting system which may affect the resulting emitted photon patterns (and require adaptation of the instructions).

The present inventors have found that the algorithm in accordance with the disclosure, wherein the algorithm is further provided with an ambient conditions feedback mechanism, as described above, may further be improved if the feedback mechanism receives input regarding the ambient conditions from a multitude of distinct locations, such as two or more, three or four or more distinct locations within the space wherein the LED lighting system operates and adapts the instructions based on said input from a multitude of distinct locations.

Thus, in preferred embodiments in accordance with the disclosure, the ambient conditions feedback mechanism is provided comprising the steps of:

receiving a first input regarding the ambient conditions at a first location, receiving a second input regarding the ambient conditions at a second location, optionally receiving a third or further input regarding the ambient conditions at a third or further location, optionally defining new subgroups, and adapting the instructions based on said first and second input and optionally based on said third or further input.

This may, for example, be especially advantageous in vertical farming applications, wherein the farm may be theoretically divided into different zones, for example in a grid-like pattern, each zone being equipped with at least one LED. The present inventors envisage the use of an algorithm in accordance with the disclosure in order to continuously vary the photon pattern such that heat dissipation may be improved and thus less cooling is required, improved plant growth is achieved and/or improved animal housing conditions are achieved. There is thus provided an algorithm in accordance with the disclosure, wherein the algorithm is further provided with an ambient conditions feedback mechanism, said ambient conditions feedback mechanism comprising the steps of:

receiving a first input regarding the ambient conditions in a first zone comprising one or more LEDs, receiving a second input regarding the ambient conditions in a second zone comprising one or more LEDs which are not comprised in the first zone, said second zone flanking the first zone, adapting the instructions based on said first and second input such that the one or more LEDs in the first zone are comprised in a first subgroup, the one or more LEDs in the second zone are comprised in a second subgroup, and the heat generated by the first subgroup is at least 20%, at least 30%, at least 50%, at least 70% lower than the heat generated by the second subgroup. In embodiments at least 50%, at least 60%, at least 70%, at least 80%, at least 90%, at least 99% or all of the LEDs comprised in the second zone are not comprised in the first zone.

Furthermore, the ambient conditions feedback mechanism may further comprise the step of instructing systems external to the LED lighting system. Such external systems may comprise at least one of a ventilation system, a heating system, a cooling system, an air (de)humidification system, and a high-voltage air ionisation system.

It will be understood by those skilled in the art that the different mechanisms, such as the response feedback mechanism, the ambient conditions feedback mechanism and the internal monitoring feedback mechanism, in practice may be combined into one feedback mechanism which takes various parameters into account.

The multicolour LED lighting system comprising at least two subgroups wherein each subgroup comprises one or more LEDs, may be provided in a variety of forms. It will be understood to the person skilled in the art that the subgroups are not necessarily fixed during execution of the algorithm. Indeed, if the LED controller is capable of sending specific instructions to each individual LED, the LED subgroups do not need to be hard-wired into the system and the subgroups may be dynamic depending on which group of LEDs is receiving the same instructions.

In an embodiment, the response feedback mechanism may comprise the steps of:

receiving input regarding the status of inducing the current desired response, optionally altering the sequence of desired responses, optionally defining new subgroups, and adapting or maintaining the instructions based on said input, wherein the step of adapting or maintaining the instructions based on said input comprises comparing by the control system 31 (FIG. 8), the received input with at least partially the input data stored in the one or more databases 25. Comparing by the control system 31 may be performed by statistical means known in the art, such as mean, median, analysis of variance, t-test, Z-test, etc.

The control system 31, may further generate output data based on the comparison of the received input with the stored input data, wherein the generated output data may comprise at least adapted or maintained instructions. In an embodiment, the output data may further comprise at least one of output signals to external systems (e.g., a ventilation system, a heating system, a cooling system, an air (de)humidification system, and/or a high-voltage air ionisation system) and/or to a user through the user interface 50, wherein the output data comprises status information of one or more animals, such as stress, disease, activity level, location, movement, etc. and/or instructions, for example to remove one or more specific animals, or to perform a certain activity in an empty area such as cleaning. Thus, the output data may be provided for effectively managing, for example, an animal facility.

In embodiments, the control system 31 may store the input data along with the corresponding output data in the one or more databases 25.

Programming

Figure 4:
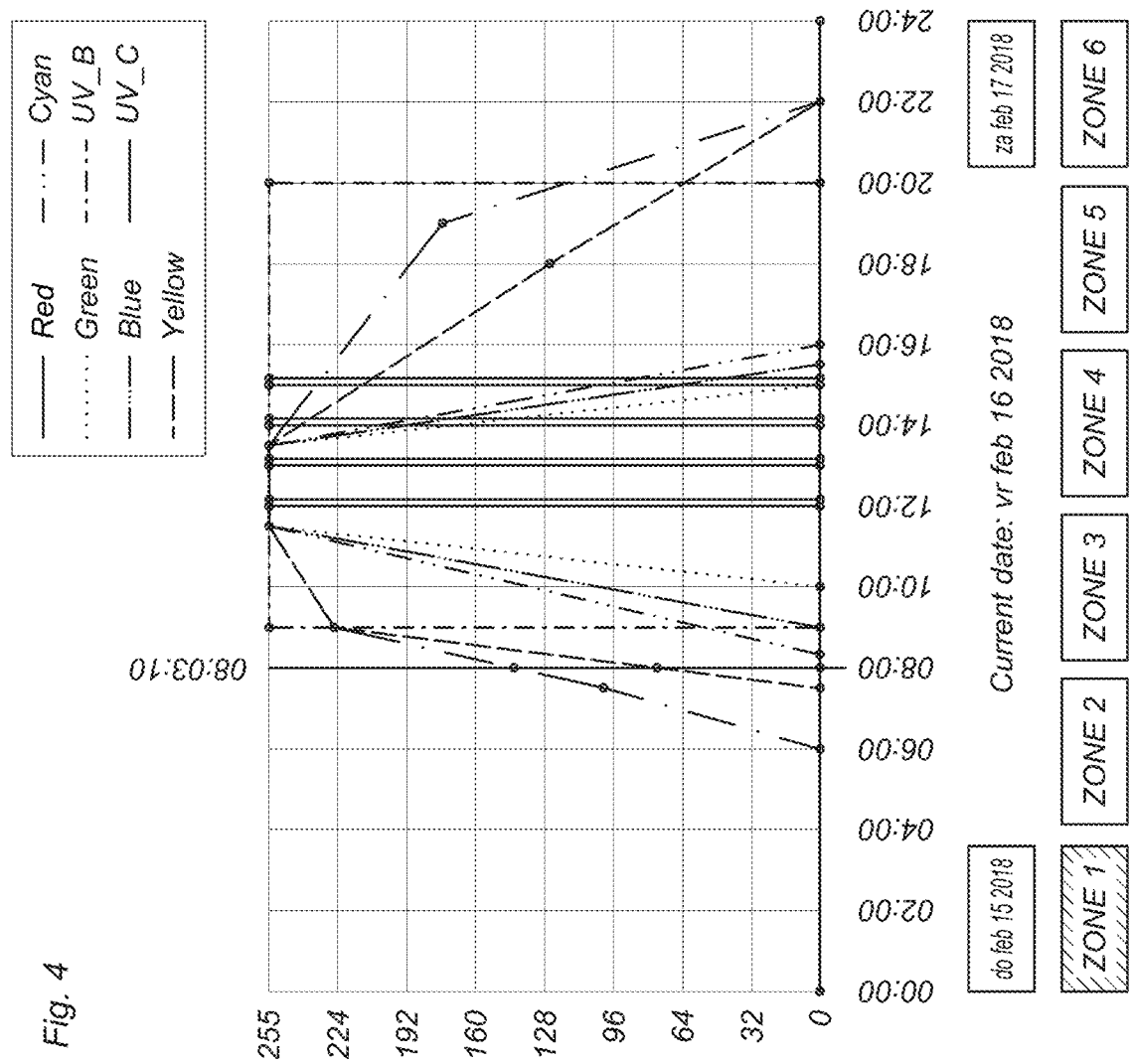
FIG. 4 shows a graphic representation of a varying or dynamic photon pattern, used in another example according to the present disclosure. The graphic representation is shown in a screen of an editor software for composing algorithms according to the present disclosure.

Algorithms according to the present disclosure may be programmed using an editor software, which may for example be similar to the screen shown in FIG. 4: with a graphic representation of the varying photon patterns on which changes of events can be sequenced. In the embodiment shown, the user can define separate intensity curves per dominant colour (e.g. red, green, blue, yellow, cyan, UV_B, UV_C), which corresponds to wavelength ranges. The graphic representation of the intensity curves may facilitate programming: a user may simply drag corners of the curve on the display to alter the photon pattern, i.e. the sequence. In the bottom right corner of the screen of FIG. 4, the current average colour at the relevant point in time is shown. In a different screen, zones or target locations in the respective facility may be defined by the user. These zones can be selected in the screen of FIG. 4 (see buttons at the bottom of the screen) for definition of the associated photon pattern.

EXAMPLES

Example 1

An example of an embodiment of the algorithm in accordance with the disclosure is shown in FIG. 1. The algorithm is provided for inducing a sequence of 2 desired responses 101 (eating) and 102 (drinking) in an animal, such as a chicken. The algorithm comprises the steps of 103 defining a first subgroup on or near feed, 104 defining a second subgroup on or near drinking water which does not overlap with the first subgroup and 105 providing instructions such that the first subgroup emits stimulating photons and the second subgroup emits unattractive photons. The algorithm is further equipped with a response feedback mechanism comprising the steps of 106 receiving input regarding the status of inducing the current desired response (eating), for example in the form of data regarding the amount of feed in the pan, for example through a weighing mechanism, or user input, 107 evaluating the status of inducing the current desired response, for example by comparison to a predefined threshold, looping back to step 105 if the threshold is not reached or continuing to step 108 and adapting the instructions to induce the second desired response if the threshold is reached.

Example 2

Figure 2:
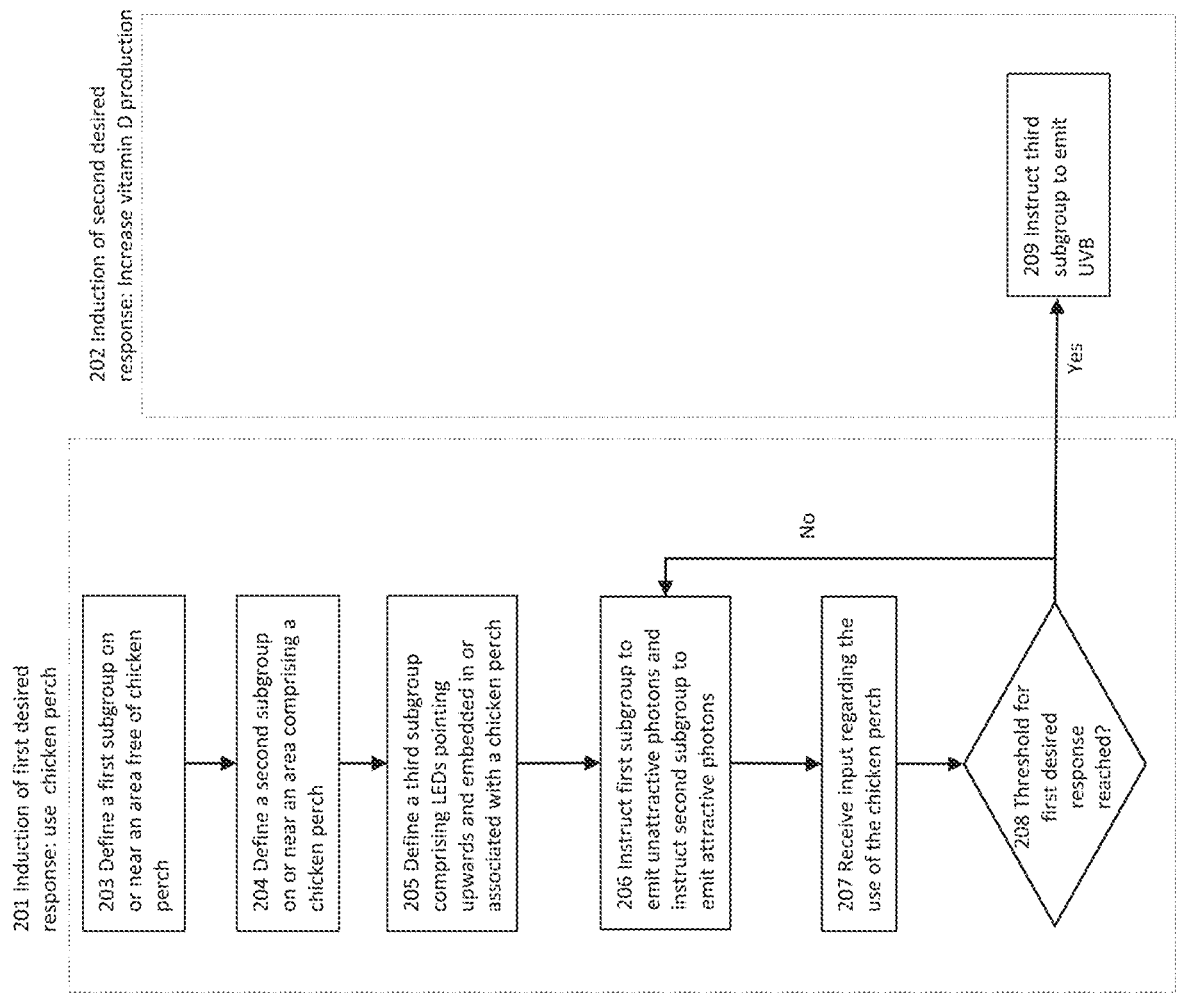
FIG. 2 shows a second example of an algorithm according to the present disclosure.

An example of an embodiment of the algorithm in accordance with the disclosure is shown in FIG. 2. It is known (see e.g. Schutkowski A, Krämer J, Kluge H, et al. *UVB Exposure of Farm Animals: Study on a Food-Based Strategy to Bridge the Gap between Current Vitamin D Intakes and Dietary Targets*. Willson R C, ed. *PLoS ONE*. 2013; 8(7): e69418. doi:10.1371/journal.pone.0069418) that most of the 7-dehydrocholesterol (7-DHC), the pre-cursor and limiting factor for vitamin $D_3$ synthesis, is located in the unfeathered skin of the chicken legs. The embodiment described in this example thus provides an inventive and energy-efficient way of achieving increased vitamin $D_3$ levels in chicken and egg. The algorithm is provided for inducing a sequence of 2 desired responses 201 (use chicken perch) and 202 (increase vitamin D production) in a chicken. The algorithm comprises the steps of 203 defining a first subgroup on or near an area free of chicken perch, 204 defining a second subgroup on or near an area comprising a chicken perch, 205 defining a third subgroup comprising LEDs pointing upwards and embedded in or associated with a chicken perch and 206 providing instructions such that the first subgroup emits unattractive photons and the second subgroup emits attractive photons. The algorithm is further equipped with a response feedback mechanism comprising the steps of 207 receiving input regarding the status of inducing the current desired response (use chicken perch) in the form of data regarding the amount of chickens on the perch, for example through a weighing mechanism, a camera with associated image recognition and analysis hardware and/or software or user input, 208 evaluating the status of inducing the current desired response, for example by comparison to a predefined threshold, looping back to step 206 if the threshold is not reached or continuing to step 209 and adapting the instructions to induce the second desired response if the threshold is reached.

Example 3

Figure 3:
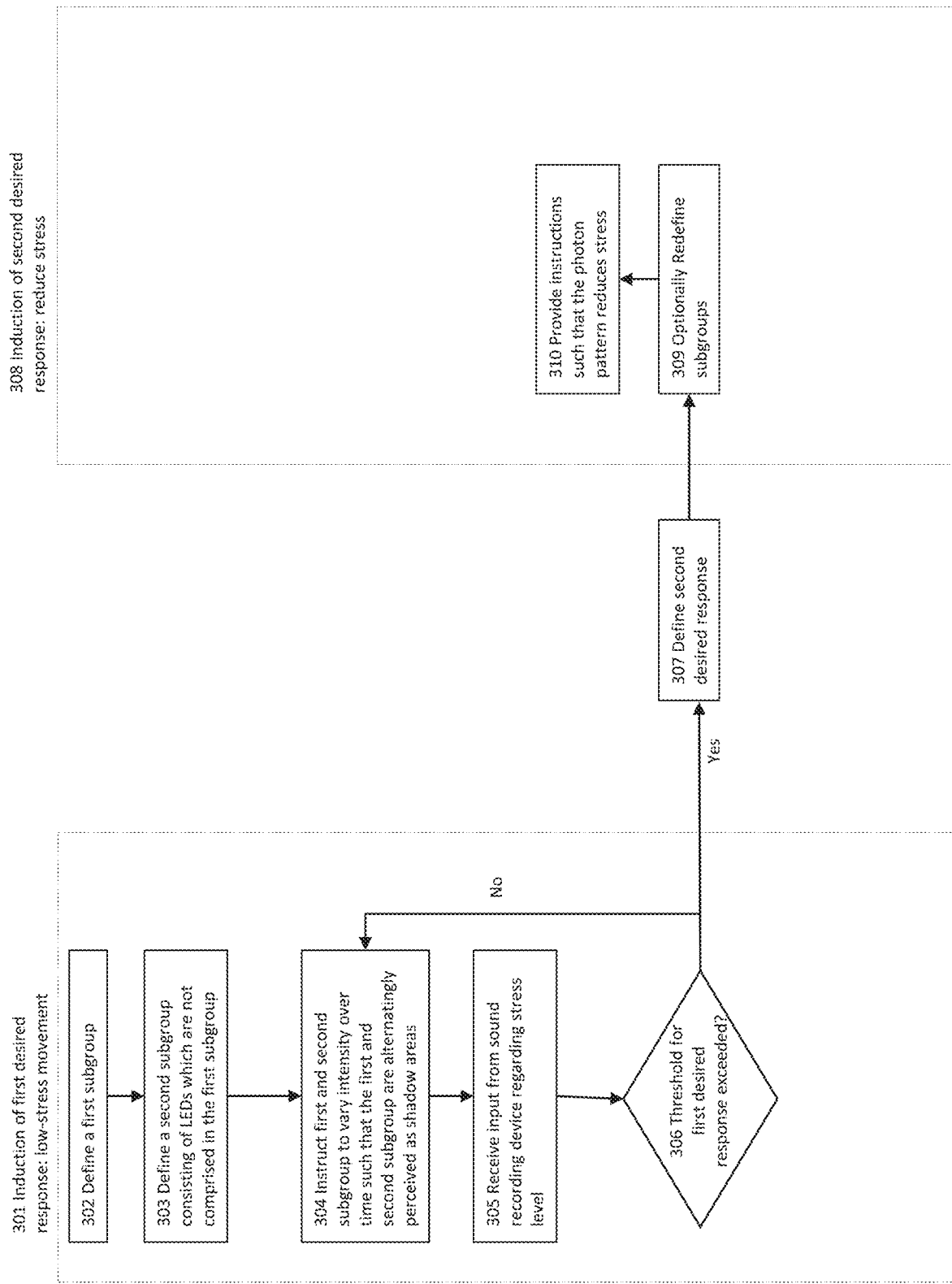
FIG. 3 shows a third example of an algorithm according to the present disclosure.

An example of an embodiment of the algorithm in accordance with the disclosure is shown in FIG. 3. The algorithm is provided for inducing a desired responses 301 (low-stress movement, which was found to reduce leg injury, as explained earlier) in an animal, such as a chicken. The algorithm comprises the steps of 303 defining a first subgroup, 304 defining a second which does not overlap with the first subgroup and 304 providing instructions such that the intensity of the photons emitted by the first and second subgroup vary over time so that the areas under the subgroups are alternatingly perceived as shadow areas. The algorithm is further equipped with a response feedback mechanism comprising the steps of 305 receiving input regarding the status of inducing the current desired response (stress-free movement), for example in the form of data from a sound-recording device, 306 evaluating the status of inducing the current desired response, for example through automated analysis of the sound identifying stress-related animal sounds, looping back to step 304 if a threshold for stress-related sounds is not reached or continuing to step 307 to define a second desired response if a high-stress situation is identified, said second desired response being to reduce stress. Step 309 allows for redefinition of subgroups and in step 310 the algorithm provides instructions to generate a photon pattern to reduce stress. The latter may be achieved by lowering the overall intensity of the photon pattern. Alternatively, if the high-stress situation is associated with fighting and/or the presence of blood on the animal or its feathers, the affected area may be drowned in red light such that the animals cannot perceive the color of the blood anymore.

Example 4

Decrease of mortality, stress and aggressive behaviour in chickens and increase in slaughter weight was achieved using an embodiment of the algorithm in accordance with the disclosure.

Example 5

Decrease in ground-laying of eggs was achieved using an algorithm in accordance with the disclosure. Use of a predetermined varying photon pattern was found to result in a reduction in the number of eggs which are laid on the ground.

Example 6

An experiment was performed wherein the algorithm in accordance with the disclosure was used to induce a sequence of desired responses comprising:
low-stress waking up
increased vitamin $D_3$ production, and
low-stress sleeping.
The photon pattern produced by the LED lighting system is shown in FIG. 4.
The experiment consisted of 4 cages of 60 chickens each which were housed under identical conditions, except for the photon pattern (according to the present disclosure, in particular FIG. 4, vs. commonly used prior art lighting) and feed (Vit $D_3$ supplemented vs. not supplemented), as shown in Table 1.

TABLE 1

Resulting egg yolk Vit $D_3$ content based on the photon pattern and feed.

| | Photon pattern | Feed | Egg yolk Vit $D_3$ content (IU/kg) |
|---|---|---|---|
| Cage 1 | According to FIG. 4 | Vit $D_3$ supplemented | 2000 |
| Cage 2 | According to FIG. 4 | Not supplemented | 930 |
| Cage 3 | Common lighting | Not supplemented | 710 |
| Cage 4 | Common lighting | Vit $D_3$ supplemented | 1600 |

Table 1 shows a remarkable increase of Vit $D_3$ content in egg yolk (25% or more) as a result of the varying photon pattern of FIG. 4 for both types of feed.

Example 7

Figure 5:
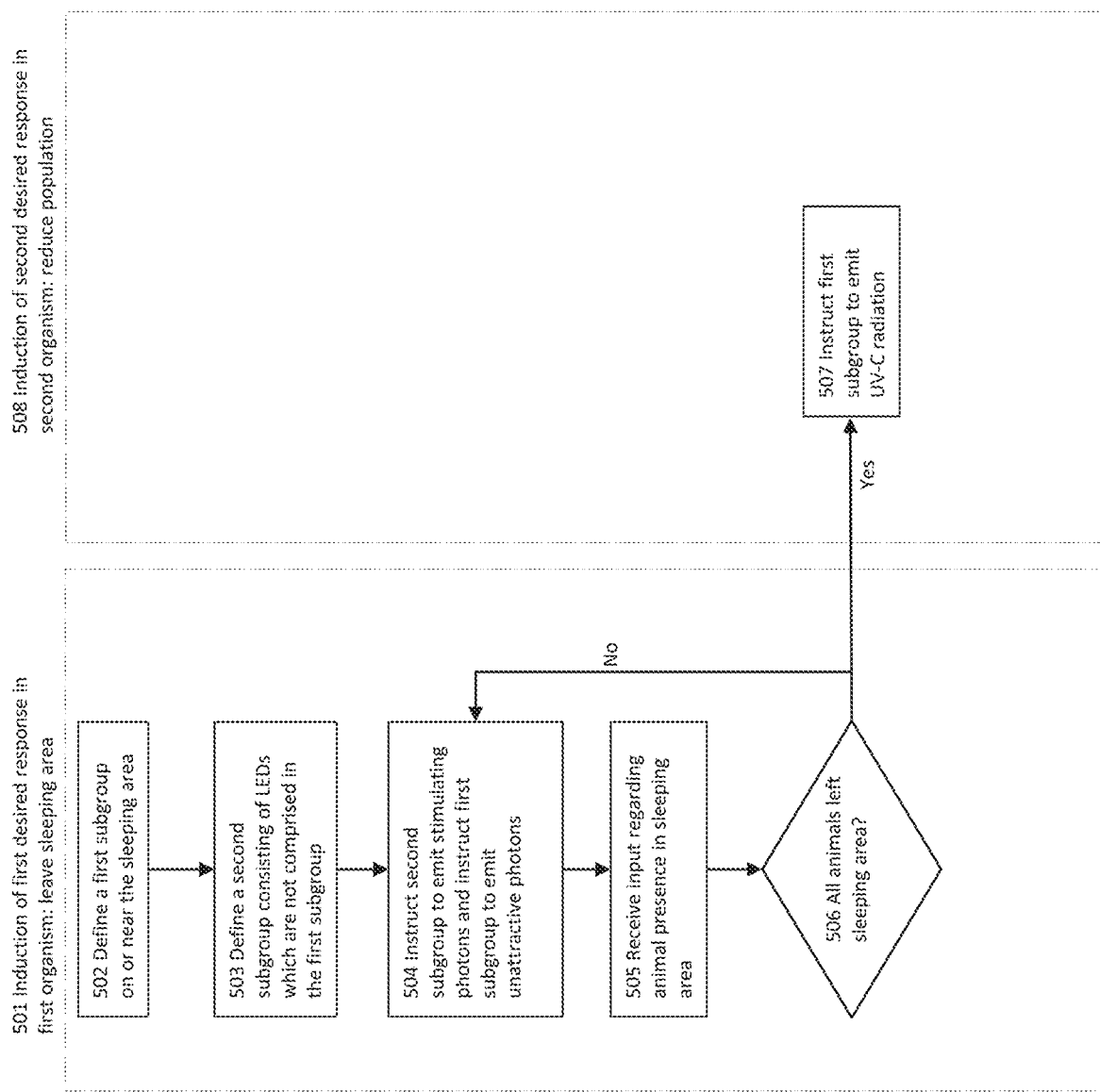
FIG. 5 shows another example of an algorithm according to the present disclosure.

An example of an embodiment of the algorithm in accordance with the disclosure is shown in FIG. 5. The algorithm is provided for inducing a sequence of 2 desired responses in 2 different organisms: 501 (leaving sleeping area) in an animal, such as a chicken and 508 (reduce population) in a pathogen, such as blood lice. The algorithm comprises the steps of 502 defining a first subgroup on or near the sleeping area, 503 defining a second subgroup which does not overlap with the first subgroup and 504 providing instructions such that the second subgroup emits stimulating photons and the first subgroup emits unattractive photons. The algorithm is further equipped with a response feedback mechanism comprising the steps of 505 receiving input regarding the status of inducing the current desired response (animal presence in sleeping area), for example through a weighing mechanism, camera system or user input, 506 evaluating the status of inducing the current desired response, for example by comparison to a predefined threshold of no animals present in the sleeping area, looping back to step 504 if the threshold is not reached or continuing to step 507 and adapting the instructions to induce the second desired response if the threshold is reached.

Example 8

Representation of Varying Photon Patterns Used in Examples 9-11

In this example, it is explained how the varying photon patterns used in examples 9-11 are represented by means of a table formatted according to Table 2.

TABLE 2

A varying photon pattern for a fictive example.

| Zone | | 1 | | | |
|---|---|---|---|---|---|
| Channel Amount | | 4 | | | |
| DMX Address | | 1 | 2 | 3 | 4 |
| Channel Names | | RED | GREEN | BLUE | WHITE |
| Channel Colors | | #FF0000 | #00FF00 | #0000FF | #FFDD00 |
| Dominant Wavelength | | 620 nm | 522 nm | 466 nm | 3000K (CCT) |
| Day | Timestamp | | | | |
| 1 Jun. 2018 | 00:00:01 | 0 | 0 | 1 | 0 |
| | 03:00:00 | 0 | | | |
| | 04:30:00 | | | | 0 |
| | 05:30:00 | 100 | | | |
| | 09:00:00 | 225 | | 1 | 225 |
| | 10:00:00 | | 0 | | |
| | 11:30:00 | 255 | 255 | 255 | 255 |
| | 13:30:00 | 255 | 255 | 255 | 255 |
| | 15:00:00 | | 0 | | |
| | 15:30:00 | | | 1 | |
| | 17:00:00 | 150 | | | |
| | 19:30:00 | 0 | | | 0 |
| | 22:00:00 | | 0 | 1 | |
| | 23:59:59 | 0 | 0 | 1 | 0 |

This recipe is specified for zone 1. A zone defines a specific LED subgroup.

The channel amount of this zone is equal to 4, meaning that there is a lamp fixture present on location which consists of 4 primary colors, each defined by their dominant wavelength. The energy for each one of these primary colors is radiated by binned LEDs, matching the desired dominant wavelength as close as possible. Multiple primaries can be combined in one LED die, or multiple single primary LEDs can be combined in one printed circuit board. Each color channel can be controlled individually on an 8 bit scale, allowing 256 different brightness levels, from 0 to 255.

An hexadecimal channel color representation is given for each color channel for representation and easy differentiation in the accompanying control software. As such, different mixtures between different color channels can be made to form uniquely composed spectra. The DMX address maps this channels data to the actual hardware device that controls the lamps.

A list of timestamped keyframes then specifies a color channels brightness level for a given time. The total of all keyframes make up a span of 24 hours. Cells without any specific value have a double function, depending on the following value of the same column. When the value is the same as the previous, the value will be kept on for the whole time span. When it differs, the value will be linearly interpolated between the start and end value over the specified time.

Certain thresholds are defined within the experimental controller application, such a minimum interpolation time of 10 sec for a full brightness range. When a brightness value of 0 jumps to a brightness value of 255 over 1 second, the actual output will always interpolate over 10 seconds. This minimum threshold ensures that sudden jumps in light level, which could cause distress, are avoided.

Looking at the example, the white channel will be dimmed between 00:00 and 04:30. From 04:30 and 09:00 it will gradually dim to level 225 (about 88% of the total output). After that it will dim to 255, or full output, until 11:30. It will remain in this state until 13:30, and will thereafter fade to 0 at 19:30. The white channel stays dimmed until 00:00. Keyframes for the next day are defined in a new table, containing possibly different values.

Example 9

Inducing Increased Movement, Decreased Footpad Dermatitis, Increased Overall Health At the Provincial Test Farm for Poultry in Geel, Belgium a test was carried out with broiler chickens. Two departments (2 sections per department, each with 1150 broiler chickens) were included in the trial. Sections A and B functioned as a control employing conventional lighting, while sections C and D employed an algorithm and a LED multicolour lighting system in accordance with the present disclosure (reduced to practice in the form of the Spectra system) with the aim of inducing responses such as increasing the overall movement of the broiler chickens, decreasing the amount of footpad dermatitis and/or increasing the overall health.

The conventional lighting used in Sections A and B included LED light of 3000 kelvin CCT, with an intensity measured on chicken-height varying between 15 and 20 lux. Light was emitted from linear fixtures hung against ceiling.

their new environment. Photon pattern 1 is shown in Table 3.

TABLE 3

Photon pattern 1

| Photon pattern 1 | | | | | | | | |
|---|---|---|---|---|---|---|---|---|
| Zone | 1 | | | | | | | |
| Channel Amount | 12 | | | | | | | |
| DMX Address | 1 | 2 | 3 | 4 | 9 | 10 | 11 | |
| Channel Names | RED | GREEN | BLUE | WHITE | RED | GREEN | BLUE | |
| Channel Color | #FF0000 | #00FF00 | #0000FF | #FFDD00 | #FF0000 | #00FF00 | #0000FF | |
| Channel Group | Water | Water | Water | Water | Food | Food | Food | |
| Dominant Wavelength | 620 nm | 520 nm | 470 nm | 3000K(CCT) | 620 nm | 520 nm | 470 nm | |

| DAYS | Timestamp | | | DATA | | | | |
|---|---|---|---|---|---|---|---|---|
| 6 Dec. 2018- | 00:00:01 | 0 | 0 | 0 | 200 | 0 | 0 | 0 |
| 9 Dec. 2018 | 05:00:00 | 0 | 0 | 0 | 200 | 0 | 0 | 0 |
|  | 05:00:01 | 0 | 0 | 0 | 0 | 0 | 0 | 0 |
|  | 08:00:00 | 0 | 0 | 0 | 0 | 0 | 0 | 0 |
|  | 08:00:01 | 0 | 0 | 0 | 200 | 0 | 0 | 0 |
|  | 18:00:00 | 0 | 0 | 0 | 200 | 0 | 0 | 0 |
|  | 18:00:01 | 0 | 0 | 0 | 0 | 0 | 0 | 0 |
|  | 21:00:00 | 0 | 0 | 0 | 0 | 0 | 0 | 0 |
|  | 21:00:01 | 0 | 0 | 0 | 200 | 0 | 0 | 0 |
|  | 23:59:59 | 0 | 0 | 0 | 200 | 0 | 0 | 0 |

| Photon pattern 1 | | | | | | |
|---|---|---|---|---|---|---|
| Zone | | | | | | |
| Channel Amount | | | | | | |
| DMX Address | | 12 | 17 | 18 | 19 | 20 |
| Channel Names | | WHITE | RED | GREEN | BLUE | WHITE |
| Channel Color | | #FFDD00 | #FF0000 | #00FF00 | #0000FF | #FFDD00 |
| Channel Group | | Food | Corridor | Corridor | Corridor | Corridor |
| Dominant Wavelength | | 3000K (CCT) | 620 nm | 520 nm | 470 nm | 3000K (CCT) |

| DAYS | Timestamp | | DATA | | | |
|---|---|---|---|---|---|---|
| 6 Dec. 2018- | 00:00:01 | 200 | 0 | 0 | 0 | 200 |
| 9 Dec. 2018 | 05:00:00 | 200 | 0 | 0 | 0 | 200 |
|  | 05:00:01 | 0 | 0 | 0 | 0 | 0 |
|  | 08:00:00 | 0 | 0 | 0 | 0 | 0 |
|  | 08:00:01 | 200 | 0 | 0 | 0 | 200 |
|  | 18:00:00 | 200 | 0 | 0 | 0 | 200 |
|  | 18:00:01 | 0 | 0 | 0 | 0 | 0 |
|  | 21:00:00 | 0 | 0 | 0 | 0 | 0 |
|  | 21:00:01 | 200 | 0 | 0 | 0 | 200 |
|  | 23:59:59 | 200 | 0 | 0 | 0 | 200 |

Each of sections C and D contained three separate controllable lighting rails, consisting of multiple RGBW color tubes. One rail was attached to the water dispenser rail (WATER), another was attached to the food dispenser (FOOD) and the last one was hung approximately 2 m above the ground, in the middle corridor of the stable (CORRIDOR). In total this accounts for 12 possible channels per section. This setup is shown in FIG. 10.

Figure 10:
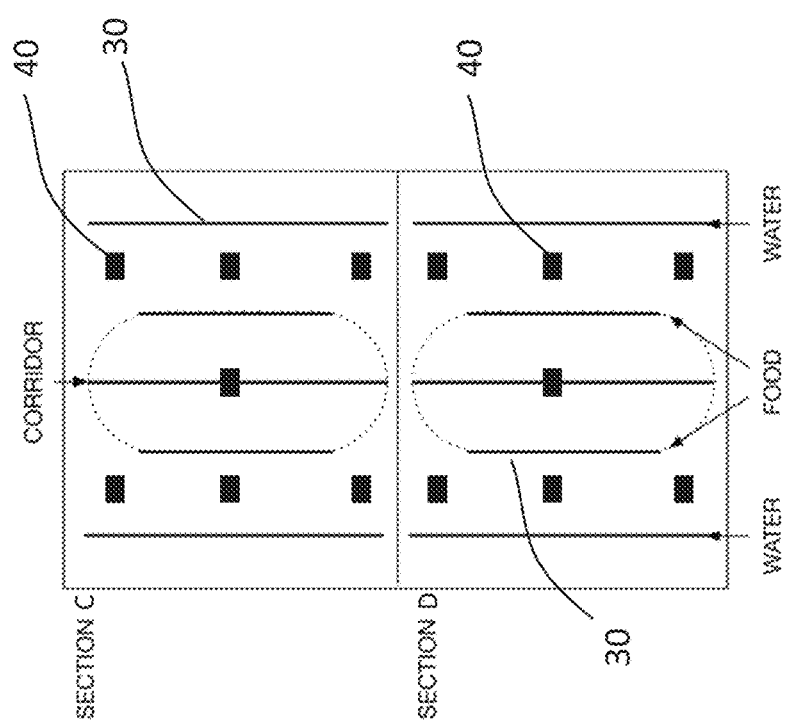

Furthermore, FIG. 10 shows an example installation of an input system 40 comprising of sensors, preferably ammonia and/or image sensors. Such sensors may be located in or near the relevant zones and/or near the LEDs or the subgroups of LEDs.

During the test 4 different predetermined photon patterns (i.e., photon patterns 1-4) were each active, for a defined period of time, after which the next recipe took over.

Photon pattern 1: The first photon pattern was active during the first four days (i.e., days Dec. 6, 2018-Dec. 9, 2018) the chickens entered the stable and gave white light, dimmed to around 78%, on the main central corridors. No variable spectrum was active. This photon pattern focused on calming the chickens and allow them to acclimatize to After four days (i.e., on day Dec. 10, 2018), photon pattern 2 was used. The second photon pattern then introduced a 1 hour color cycle. This color cycle was used as the basic building block for the remaining duration of the experimental test. The cycle was first introduced at 10:00 and 14:00, in order for the chickens to get accustomed to light variation. The color cycle was defined as shown in Table 4.

TABLE 4

| One hour color cycle | | | | |
|---|---|---|---|---|
| | 1 HOUR | | | |
| | 0-10 m | 10 m-20 m | 20 m-30 m | 30 m-60 m |
| WATER | blue | red-white | blue | OFF |
| FOOD | red-white | blue | red-white | OFF |
| CORRIDOR | OFF | OFF | OFF | special white |

It was experimented with blue light to mark a "no-go" zone for the animals while the other zone was made attrac tive with warm reddish white light. Table 4 shows that the food zone was made attractive twice, while the water zone once. Each food or drink period lasted for 10 minutes. After 30 mins, the water and food light turned off and a special light (mixture of warm white and cyan) was given through the corridor lights for 30 mins. This completed the 1 hour cycle, which was then repeated depending on light hours or dark hours in the stable.

Photon pattern 2, which introduced this 1 hour color cycle, was repeated for 3 subsequent days (e.g., days Dec. 10, 2018-Dec. 12, 2018). An example of photon pattern 2 is shown in Table 5.

TABLE 5

Photon pattern 2

| Photon pattern 2 | | | | | | | | |
|---|---|---|---|---|---|---|---|---|
| Zone | | 1 | | | | | | |
| Channel Amount | | 12 | | | | | | |
| DMX Address | | 1 | 2 | 3 | 4 | 9 | 10 | 11 |
| Channel Names | | RED | GREEN | BLUE | WHITE | RED | GREEN | BLUE |
| Channel Color | | #FF0000 | #00FF00 | #0000FF | #FFDD00 | #FF0000 | #00FF00 | #0000FF |
| Channel Group | | Water | Water | Water | Water | Food | Food | Food |
| Dominant Wavelength | | 620 nm | 520 nm | 470 nm | 3000K (CCT) | 620 nm | 520 nm | 470 nm |
| DAYS | Timestamp | | | | DATA | | | |
| 10 Dec. 2018- 12 Dec. 2018 | 00:00:01 | 0 | 0 | 0 | 200 | 0 | 0 | 0 |
| | 05:00:00 | | | | 200 | | | |
| | 05:00:01 | | | | 0 | | | |
| | 08:00:00 | | | | 0 | | | |
| | 08:00:01 | | | | 200 | | | |
| | 10:00:00 | 0 | 0 | 0 | 200 | 0 | 0 | 0 |
| | 10:01:00 | | | 255 | 0 | 255 | | |
| | 10:10:00 | 0 | | 255 | 0 | 255 | | 0 |
| | 10:11:00 | 255 | | 0 | 200 | | | 255 |
| | 10:20:00 | 255 | | 0 | 200 | | | 255 |
| | 10:21:00 | 0 | | 255 | 0 | 255 | | 0 |
| | 10:30:00 | | | 255 | | 255 | | |
| | 10:31:00 | | | 0 | | 0 | | |
| | 10:33:00 | | | | | | | |
| | 10:35:00 | | | | | | | |
| | 10:57:00 | | | | | | | |
| | 10:59:00 | | | | 0 | | | |
| | 11:00:00 | | | | 200 | | | |
| | 14:00:00 | | | 0 | 200 | 0 | | |
| | 14:01:00 | | | 255 | 0 | 255 | | |
| | 14:10:00 | 0 | | 255 | 0 | 255 | | 0 |
| | 14:11:00 | 255 | | 0 | 200 | | | 255 |
| | 14:20:00 | 255 | | 0 | 200 | | | 255 |
| | 14:21:00 | 0 | | 255 | 0 | 255 | | 0 |
| | 14:30:00 | | | 255 | | 255 | | |
| | 14:31:00 | | | 0 | | 0 | | |
| | 14:33:00 | | | | | | | |
| | 14:35:00 | | | | | | | |
| | 14:57:00 | | | | | | | |
| | 14:59:00 | | | | 0 | | | |
| | 15:00:00 | | | | 200 | | | |
| | 18:00:00 | 0 | 0 | 0 | 200 | 0 | 0 | 0 |
| | 18:00:01 | 0 | 0 | 0 | 0 | 0 | 0 | 0 |
| | 21:00:00 | 0 | 0 | 0 | 0 | 0 | 0 | 0 |
| | 21:00:01 | 0 | 0 | 0 | 200 | 0 | 0 | 0 |
| | 23:59:59 | 0 | 0 | 0 | 200 | 0 | 0 | 0 |

| Photon pattern 2 | | | | | | |
|---|---|---|---|---|---|---|
| Zone | | | | | | |
| Channel Amount | | | | | | |
| DMX Address | | 12 | 17 | 18 | 19 | 20 |
| Channel Names | | WHITE | RED | GREEN | BLUE | WHITE |
| Channel Color | | #FFDD00 | #FF0000 | #00FF00 | #0000FF | #FFDD00 |
| Channel Group | | Food | Corridor | Corridor | Corridor | Corridor |
| Dominant Wavelength | | 3000K (CCT) | 620 nm | 520 nm | 470 nm | 3000K (CCT) |
| DAYS | Timestamp | | | DATA | | |
| 10 Dec. 2018- 12 Dec. 2018 | 00:00:01 | 200 | 0 | 0 | 0 | 200 |
| | 05:00:00 | 200 | | | | 200 |
| | 05:00:01 | 0 | | | | 0 |
| | 08:00:00 | 0 | | | | 0 |
| | 08:00:01 | 200 | | | | 200 |
| | 10:00:00 | | 0 | 0 | 0 | 200 |
| | 10:01:00 | 200 | | | | 0 |

TABLE 5-continued

| Photon pattern 2 | | | | | |
|---|---|---|---|---|---|
| 10:10:00 | 200 | | | | |
| 10:11:00 | 0 | | | | |
| 10:20:00 | 0 | | | | |
| 10:21:00 | 200 | | | | |
| 10:30:00 | 200 | 0 | | | |
| 10:31:00 | 0 | 200 | 0 | | 0 |
| 10:33:00 | | | 255 | | |
| 10:35:00 | | | | | 200 |
| 10:57:00 | | | 255 | | |
| 10:59:00 | 0 | 200 | 0 | | |
| 11:00:00 | 200 | 0 | | | 200 |
| 14:00:00 | | | | | 200 |
| 14:01:00 | 200 | | | | 0 |
| 14:10:00 | 200 | | | | |
| 14:11:00 | 0 | | | | |
| 14:20:00 | 0 | | | | |
| 14:21:00 | 200 | | | | |
| 14:30:00 | 200 | 0 | | | 0 |
| 14:31:00 | 0 | 200 | 0 | | 0 |
| 14:33:00 | | | 255 | | |
| 14:35:00 | | | | | 200 |
| 14:57:00 | | | 255 | | |
| 14:59:00 | 0 | 200 | 0 | | |
| 15:00:00 | 200 | 0 | | | 200 |
| 18:00:00 | 200 | 0 | 0 | 0 | 200 |
| 18:00:01 | 0 | 0 | 0 | 0 | 0 |
| 21:00:00 | 0 | 0 | 0 | 0 | 0 |
| 21:00:01 | 200 | 0 | 0 | 0 | 200 |
| 23:59:59 | 200 | 0 | 0 | 0 | 200 |

After three days running photon pattern 2, photon pattern 3 was applied where the 1 hour color cycle was multiplied over the whole day, as can be seen in the following overview in Table 6.

TABLE 6

Overview of photon pattern 3

| HOUR | LIGHT |
|---|---|
| 00:00 | DARK |
| 01:00 | DARK |
| 02:00 | DARK |
| 03:00 | COLOR CYCLE |
| 04:00 | COLOR CYCLE |
| 05:00 | COLOR CYCLE |
| 06:00 | COLOR CYCLE |
| 07:00 | DARK |
| 08:00 | COLOR CYCLE |
| 09:00 | COLOR CYCLE |
| 10:00 | COLOR CYCLE |
| 11:00 | COLOR CYCLE |

TABLE 6-continued

Overview of photon pattern 3

| HOUR | LIGHT |
|---|---|
| 12:00 | COLOR CYCLE |
| 13:00 | COLOR CYCLE |
| 14:00 | COLOR CYCLE |
| 15:00 | COLOR CYCLE |
| 16:00 | COLOR CYCLE |
| 17:00 | COLOR CYCLE |
| 18:00 | COLOR CYCLE |
| 19:00 | COLOR CYCLE |
| 20:00 | DARK |
| 21:00 | COLOR CYCLE |
| 22:00 | COLOR CYCLE |
| 23:00 | COLOR CYCLE |

Photon pattern 3 (summarized in the Tables 7 and 8) was used for 14 days (i.e., days Dec. 13, 2018-Dec. 26, 2018).

Each "DARK" timeblock was as shown in Table 7 (exemplified for hour 00:00), i.e. no light was used.

TABLE 7

| "DARK" timeblock | | | | | | |
|---|---|---|---|---|---|---|
| | RED #FF0000 Water | GREEN #00FF00 Water | BLUE #0000FF Water | WHITE #FFDD00 Water | RED #FF0000 Food | GREEN #00FF00 Food |
| 00:00:01 | 0 | 0 | 0 | 0 | 0 | 0 |
| 01:00:00 | 0 | 0 | 0 | 0 | 0 | 0 |
| | BLUE #0000FF Food | WHITE #FFDD00 Food | RED #FF0000 Corridor | GREEN #00FF00 Corridor | BLUE #0000FF Corridor | WHITE #FFDD00 Corridor |
| 00:00:01 | 0 | 0 | 0 | 0 | 0 | 0 |
| 01:00:00 | 0 | 0 | 0 | 0 | 0 | 0 |

Each "COLOR CYCLE" timeblock was as shown in Table 8 (exemplified for hour 04:00).

TABLE 8

"COLOR CYCLE" timeblock

| | RED #FF0000 Water | GREEN #00FF00 Water | BLUE #0000FF Water | WHITE #FFDD00 Water | RED #FF0000 Food | GREEN #00FF00 Food |
|---|---|---|---|---|---|---|
| 04:00:00 | 0 | 0 | 0 | 0 | 0 | 0 |
| 04:01:00 | | | 255 | 0 | 255 | |
| 04:10:00 | 0 | | 255 | 0 | 255 | |
| 04:11:00 | 255 | | 0 | 255 | 0 | |
| 04:20:00 | 255 | | 0 | 255 | 0 | |
| 04:21:00 | 0 | | 255 | 0 | 255 | |
| 04:30:00 | | | 255 | 0 | 255 | |
| 04:31:00 | 0 | 0 | 0 | 0 | 0 | 0 |
| 05:00:00 | 0 | 0 | 0 | 0 | 0 | 0 |

| | BLUE #0000FF Food | WHITE #FFDD00 Food | RED #FF0000 Corridor | GREEN #00FF00 Corridor | BLUE #0000FF Corridor | WHITE #FFDD00 Corridor |
|---|---|---|---|---|---|---|
| 04:00:00 | 0 | 0 | 0 | 0 | 0 | 0 |
| 04:01:00 | | 255 | | | | 0 |
| 04:10:00 | 0 | 255 | | | | |
| 04:11:00 | 255 | 0 | | | | |
| 04:20:00 | 255 | 0 | | | | |
| 04:21:00 | 0 | 255 | | | | |
| 04:30:00 | | 255 | | 0 | | 0 |
| 04:31:00 | 0 | 0 | | 255 | | 50 |
| 05:00:00 | 0 | 0 | 0 | 255 | 0 | 50 |

After 14 days of running photon pattern 3, photon pattern 4 was used for 20 days (i.e., days Dec. 27, 2018-Jan. 15, 2019) until the chickens were taken out of their respective sections. Photon pattern 4 corresponds to photon pattern 3 wherein the corridor lights stayed ON at 1 unit blue (about 0.4% of the maximum intensity) during the dark timeblocks.

Results: During the experiment a visibly higher activity was observed with poultry in section C and D as compared to A and B. To assess the higher activity on footpad dermatitis (FPD) scores and hockburn (HB) scores were calculated in all sections for the day of unloading (i.e., after 41 days, in this experiment on day Jan. 16, 2019). The Swedish system (see Berg, C. (1998), *Foot-pad dermatitis in broilers and turkeys*. Doctoral diss. Dept. of Animal Environment and Health, SLU. Acta Universitatis Agriculturae Sueciae, Sweden) was used for assigning FPD scores. This system is a three tier scoring system as is known (see Dr. de Jong I., Ing. van Harn J. (2012), *Management Tools to Reduce Footpad Dermatitis in Broilers*), wherein a score of 0 represents no lesions, no or very small superficial lesions, mild hyperkeratosis (thickening of the outer layer of the skin) or healed lesion; a score of 1 represents mild lesion, superficial lesions, dark papillae and hyperkeratosis; and a score of 2 represents severe lesion; epidermis is affected, ulcers or scabs, signs of haemorrhages or swollen footpads. A three-tier scoring system (see e.g., Tucker, S. A., & Walker, A. W. (1992). *Hock Burn In Broilers. Recent Advances in Animal Nutrition*, 33-50) was used for assigning HB scores, wherein a score of 0 represents no discolouration; a score of 1 represents discolouration with small scab(s); a score of 2 represents enlarged hock with large scab(s).

As shown in Table 9, the footpad dermatitis scores, which is an important parameter for animal welfare with broiler chickens, for sections C and D are 50% reduced as compared to A and B. This shows that there is an increase in quality of the feet of the broiler chickens in sections when a varying photon pattern in accordance with the invention is used. In addition, the hock burn scores for sections C and D are also more than 50% reduced. It was observed that the bedding material was dryer, indicating lower risk of FPD and/or HB. It was further observed that a thinner bedding, such as 1.0 vs. 2.0 kg/m$^2$ or 1.5 vs. 2.0 kg/m$^2$ of chopped wheat straw, can be used resulting in lower costs on the facility.

TABLE 9

Footpad dermatitis (FPD) scores and hockburn (HB) scores

| Section | FPD0 | FPD1 | FPD2 | FPD score | HB0 | HB1 | HB2 | HB score |
|---|---|---|---|---|---|---|---|---|
| A | 9 | 20 | 21 | 52 | 6 | 19 | 0 | 9.5 |
| B | 5 | 19 | 26 | 61.5 | 6 | 19 | 0 | 9.5 |
| C | 26 | 16 | 8 | 24 | 21 | 4 | 0 | 2 |
| D | 22 | 17 | 11 | 30.5 | 17 | 8 | 0 | 4 |

In order to assess the impact of the increased activity and improved animal welfare parameters such as the FPD and HB on productivity, the feed conversion rate and mortality was calculated. As can be seen from Table 10, the use of an algorithm and LED lighting system in accordance with the invention achieves improved activity and overall well-being in poultry without any significant negative effects on productivity.

TABLE 10

Effect of using an algorithm and LED lighting system in accordance with the invention

| Section | Average weight (g) | Net Feed conversion rate | Mortality rate |
|---|---|---|---|
| A | 2452.2 | 1.504 | 3.04 |
| B | 2444.3 | 1.460 | 2.70 |
| C | 2421.6 | 1.503 | 2.87 |
| D | 2367.6 | 1.500 | 2.17 |

In another experiment, water consumption monitoring devices, particularly flow sensors, were used to measure the amount of water flowing through the water dispenser to the poultry (i.e., the amount of water consumed by the poultry) in real time during each of the one-hour cycle (shown in Table 4).

Figure 13:
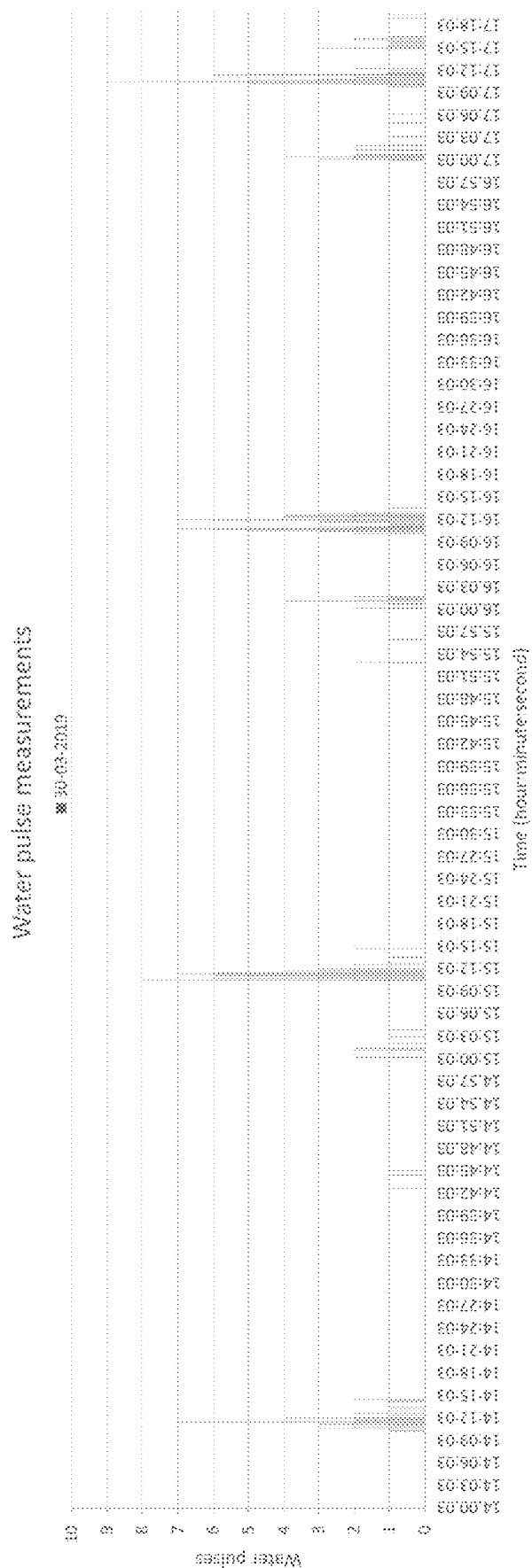
FIG. 13 shows a graphical representation of results of water pulse measurements in the experiment described with reference to FIG. 10.

For readability purposes of the results, FIG. 13 shows sample measurements in 3-minute intervals (between 14:00:03 and 17:18:03) of water pulses, where each pulse was quantified to be 2.25 mL. As shown in FIG. 13, it is observed that the photon pattern attracted the poultry to the water dispenser during 10 m-20 m in each of the one-hour cycle used in the photon pattern (e.g. photon pattern 2, 3 or 4), and drove them away from it during the time other than 10 m-20 m (i.e., 0 m-10 m, 20 m-30 m, and 30 m-60 m) in each of the one-hour cycle used in the photon pattern.

Example 10

Decrease in the Number of Ground Eggs and Increase in Number of Eggs

At the Provincial Test Farm for Poultry in Geel, Belgium a test was carried out with layer chickens. The purpose of this trial was to investigate whether the number of ground eggs could be reduced, and whether the number of eggs produced by chicken could be increased, using an algorithm and LED lighting system employing a varying photon pattern in accordance with the present disclosure (reduced to practice in the form of the Spectra system). Ground eggs occurs when chickens lay their eggs too far away from the conveyor belt, resulting in eggs that have to gathered through (expensive) human intervention. A chicken coop comprising 5 sections (with approximately 8600 layer hens per section) was used in the trial. A chicken coop containing the same number of chickens originating from the same breeding facility, having received identical vaccinations, receiving identical feed and housed under identical conditions (except for the lighting) was used as a control.

Figure 11:
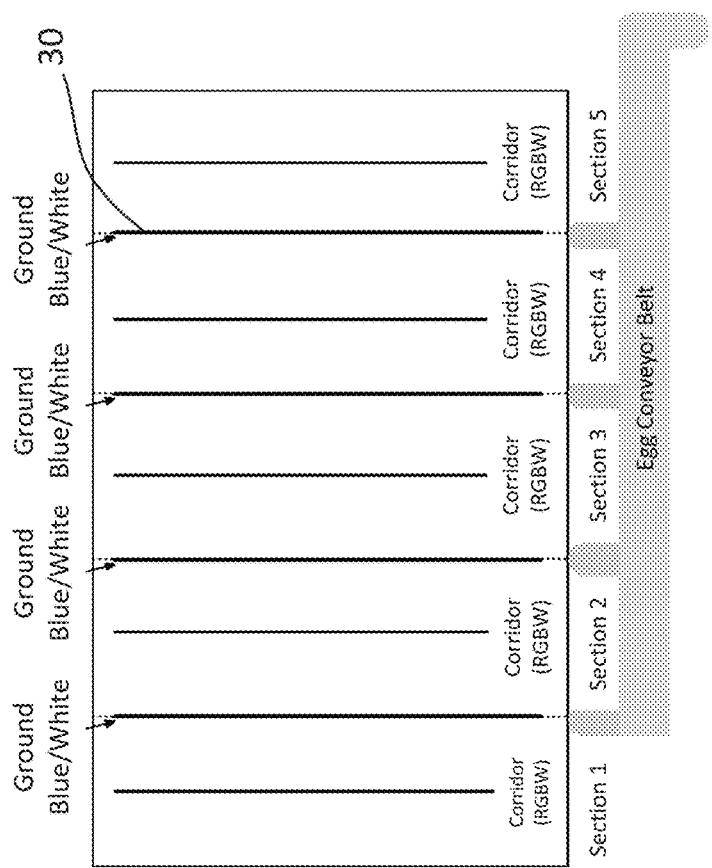
FIGS. 10 and 11 show schematic views of experimental sections employed with an algorithm and a LED multicolour lighting system in accordance with the present disclosure.

As shown in FIG. 11, each of the 5 experimental sections contained one separate controllable lighting rail hung against the roof of the corridor for each section, consisting of multiple interconnected RGB+(warm)W color tubes. A complementary system of a dual color blue/warm white lamp was hung at the ground level of each section. These lamps are referenced as 'BLUE GROUND' and 'WHITE GROUND'. The lamps were active from the start until the end of the chickens lifecycle (14 months).

Three different varying photon patterns were used during the test. Each photon pattern was used for a defined period of time, after which the next photon pattern took over. A lifecycle of layer hens takes a much longer time compared to a broiler chicken lifecycle, thus the varying photon pattern was designed to take into account the shift in dominant wavelengths which occurs in natural sunlight throughout the day.

The complementary added blue/white systems were installed as an attempt to reduce the of ground eggs by alternating blue and white light on the ground level of the stable. Blue light was given in the morning to encourage the chickens to go to the conveyor belt and lay their eggs on the conveyor belt and to stay out of the remaining space, lighted blue. After mid-day, the system switched to white to allow free ranging across the whole area.

Photon pattern 1, shown in Table 11, employed a base system of light and dark hours. The light hours start at 6:00 and stops at 19:00. The system will gradually start with a red and warm white spectrum, holding a full spectrum between 11:00 and 14:30. The system then gradually fades out the green/blue contribution to the spectrum and thereafter the red/warm white contribution to the spectrum. At dark hours, the light stays on at 1 unit blue (~0.4% light). The complementary ground system will give maximum blue light in the morning, following the start of the above cycle and lasting until 12:00. It will switch to maximum warm white light on 12:01 and remain as such until end of the above cycle. Photon pattern 1 was used for 29 days (i.e., days Dec. 19, 2017-Jan. 16, 2018).

TABLE 11

Photon pattern 1

Photon pattern 1

| | | | | | | |
|---|---|---|---|---|---|---|
| Zone | 1 | | | | | |
| Channel Amount | 6 | | | | | |
| DMX Address | 1 | 2 | 3 | 4 | 5 | 6 |
| Channel Names | RED | GREEN | BLUE | WHITE | BLUE GROUND | WHITE GROUND |
| Channel Colors | #FF0000 | #00FF00 | #0000FF | #FFDD00 | #009CFF | #FFE051 |
| Dominant Wavelength | 620 nm | 520 nm | 470 nm | 3000K (CCT) | 470 nm | 3000K (CCT) |

| Days | Timestamp | | | | | | |
|---|---|---|---|---|---|---|---|
| 19 Dec. 2017–16 Jan. 2018 | 00:00:01 | 0 | 0 | 1 | 0 | 0 | 0 |
| | 06:00:00 | 0 | | | 0 | 0 | |
| | 06:05:00 | | | | | 255 | |
| | 06:30:00 | | | | 0 | | |
| | 08:30:00 | 225 | | 1 | 225 | | |
| | 09:00:00 | | 0 | | | | |
| | 11:00:00 | 255 | 255 | 255 | 255 | | |
| | 12:00:00 | | | | | 255 | 0 |
| | 12:00:01 | | | | | 0 | 255 |
| | 14:30:00 | 255 | 255 | 255 | 255 | | |
| | 16:00:00 | | 0 | | | | |
| | 16:30:00 | | | 1 | | | |
| | 18:30:00 | | | | 0 | | 255 |
| | 19:00:00 | 0 | | | | | 0 |
| | 23:59:59 | 0 | 0 | 1 | 0 | 0 | 0 |

Photon pattern 2 (shown in Table 12) uses the same cycle as photon pattern 1 but adds one light hour at the end of the day. The complementary ground system will follow this alteration and will last one hour longer. Photon pattern 2 was used for 13 days (i.e., days Jan. 17, 2018-Jan. 29, 2018).

Results: When the layer hens were 47 weeks old, the LED lighting system according to the invention was placed in one section, and the photon patterns described above were applied. The obtained results were compared to a section employing conventional lighting. The conventional lighting

TABLE 12

Photon pattern 2

Photon pattern 2

| | | | | | | |
|---|---|---|---|---|---|---|
| Zone | 1 | | | | | |
| Channel Amount | 6 | | | | | |
| DMX Address | 1 | 2 | 3 | 4 | 5 | 6 |
| Channel Names | RED | GREEN | BLUE | WHITE | BLUE GROUND | WHITE GROUND |
| Channel Colors | #FF0000 | #00FF00 | #0000FF | #FFDD00 | #009CFF | #FFE051 |
| Dominant Wavelength | 620 nm | 520 nm | 470 nm | 3000K (CCT) | 470 nm | 3000K (CCT) |

| Days | Timestamp | | | | | | |
|---|---|---|---|---|---|---|---|
| 17 Jan. 2018- 29 Jan. 2018 | 00:00:01 | 0 | 0 | 1 | 0 | 0 | 0 |
| | 06:00:00 | 0 | | | 0 | 0 | |
| | 06:05:00 | | | | | 255 | |
| | 06:30:00 | | | | 0 | | |
| | 08:30:00 | 225 | | 1 | 225 | | |
| | 09:00:00 | | 0 | | | | |
| | 11:00:00 | 255 | 255 | 255 | 255 | | |
| | 12:00:00 | | | | | 255 | 0 |
| | 12:00:01 | | | | | 0 | 255 |
| | 15:30:00 | 255 | 255 | 255 | 255 | | |
| | 17:00:00 | | 0 | | | | |
| | 17:30:00 | | | 1 | | | |
| | 19:30:00 | | | | 0 | | 255 |
| | 20:00:00 | 0 | | | | | 0 |
| | 23:59:59 | 0 | 0 | 1 | 0 | 0 | 0 |

Photon pattern 3 (shown in Table 13) uses the same cycle as defined in recipe 2 but adds one light hour at the beginning of the day. The complementary ground system will follow this alteration and will last one hour longer. Photon pattern 1 was used for 147 days (i.e., days Jan. 30, 2018-Jun. 26, 2018).

included LED light of 3000 kelvin CCT, with an intensity measured on chicken-height varying between 15 and 20 lux. Light was emitted from linear fixtures hung against ceiling. In the section with the LED Lighting system, ground eggs disappeared almost within 2 weeks. The amount of ground eggs was reduced from approximately 3000 daily average to

TABLE 13

Photon pattern 3

Photon pattern 3

| | | | | | | |
|---|---|---|---|---|---|---|
| Zone | 1 | | | | | |
| Channel Amount | 6 | | | | | |
| DMX Address | 1 | 2 | 3 | 4 | 5 | 6 |
| Channel Names | RED | GREEN | BLUE | WHITE | BLUE GROUND | WHITE GROUND |
| Channel Colors | #FF0000 | #00FF00 | #0000FF | #FFDD00 | #009CFF | #FFE051 |
| Dominant Wavelength | 620 nm | 520 nm | 470 nm | 3000K (CCT) | 470 nm | 3000K (CCT) |

Figure 12:
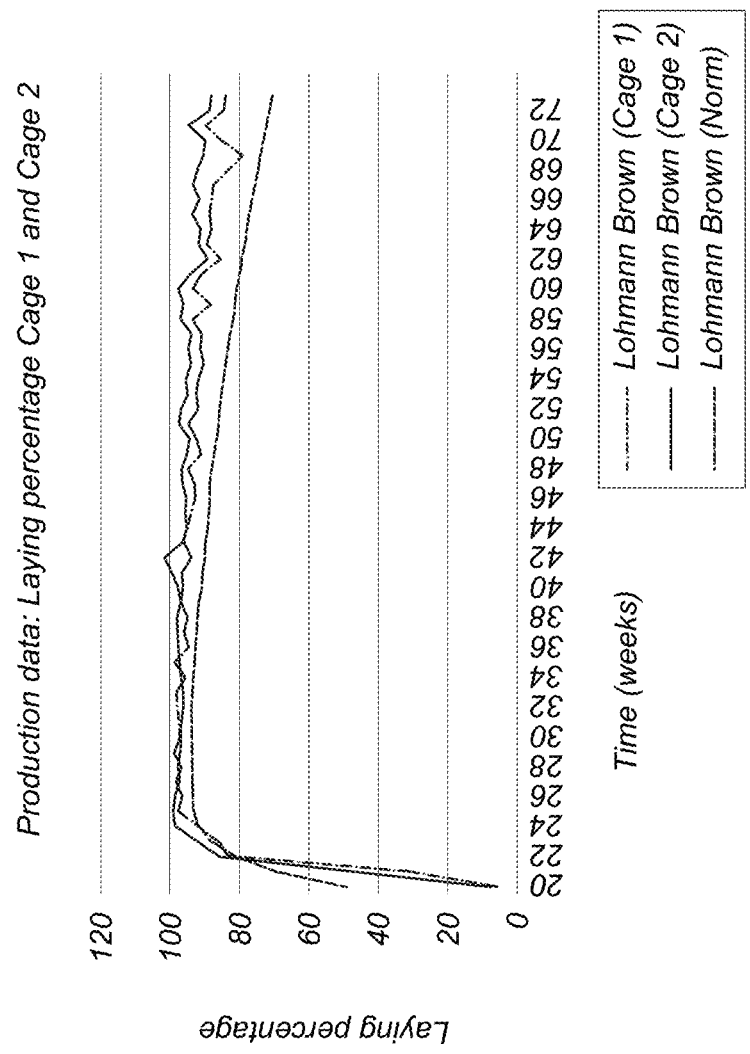
FIG. 12 shows a graphical representation of results of the experiment described with reference to FIG. 11.

| Days | Timestamp | | | | | | |
|---|---|---|---|---|---|---|---|
| 30 Jan. 2018- 26 Jun. 2018 | 00:00:01 | 0 | 0 | 1 | 0 | 0 | 0 |
| | 05:00:00 | 0 | | | 0 | 0 | |
| | 05:05:00 | | | | | 255 | |
| | 05:30:00 | | | | 0 | | |
| | 07:30:00 | 225 | | 1 | 225 | | |
| | 08:00:00 | | 0 | | | | |
| | 10:00:00 | 255 | 255 | 255 | 255 | | |
| | 12:00:00 | | | | | 255 | 0 |
| | 12:00:01 | | | | | 0 | 255 |
| | 15:30:00 | 255 | 255 | 255 | 255 | | |
| | 17:00:00 | | 0 | | | | |
| | 17:30:00 | | | 1 | | | |
| | 19:30:00 | | | | 0 | | 255 |
| | 20:00:00 | 0 | | | | | 0 |
| | 23:59:59 | 0 | 0 | 1 | 0 | 0 | 0 | approximately 150 daily average in this period. In addition the amount of laid eggs increased as compared to the section without influence of the light. Before the LED lighting system according to the invention was installed in week 47, there is a strong similarity between the production of both sections. However, after the photon patterns are applied, there is a significant increase in egg production in the sections employing the algorithms in accordance with the invention. This is shown in FIG. 12. The results were analyzed by the independent statistics agency PeHeStat, resulting in the conclusion that between week 47 and 73 there is an average increased production of 8.26 eggs per hen as compared to the reference section. Finally, the present inventors have observed that the eggs produced under the influence of the algorithm in accordance with the invention have a stronger/thicker shell, thereby ensuring that the eggs are graded as class 'A' eggs according to European standards and reducing the risk of breaking during transportation. The shell strength was measured by a device, such as Eggshell Force Gauge Model-II, and the shell thickness was determined by using an electronic micrometer with an accuracy of 0.001 mm, being measured in the middle of shell.

Example 11

Increase in Vitamin $D_3$ Content of Eggs

At Jan Noorlander in Barneveld, the Netherlands, a test was carried out with layer chickens. The purpose of this trial was to investigate whether improvements in the vitamin $D_3$ content of eggs could be achieved employing an algorithm and LED lighting system in accordance with the present disclosure. Four sections with approximately 40 layer hens per section were included in the trial. Two sections were equipped with the LED lighting system in accordance with the present disclosure (reduced to practice in the form of the Spectra system), wherein one section the layer chicken were given standard feed (section 1), whereas in the other section the same feed was supplemented with increased levels of Iodine, selenium, folic acid, Vit E, Vit B12, lutein and omega 3 and the maximum allowable level of vitamin $D_3$ (section 2) of 0.125 mg of vitamin $D_3$ per 1 Kg of feed. The other 2 sections had conventional light, wherein also one section the layer chicken were given vitamin $D_3$ supplemented feed (section 3) and in the other standard feed (section 4).

Sections 1 and 2 contained one controllable lighting fixture hung in the middle of the roof. The fixture consisted of a custom designed pcb with distinct spectral LED emitters. The system was provided with R, G, B, Warm White, Cyan, UV-A and UV-C emitters.

The lamps were active from week 18 until the end of the chickens lifecycle (78 weeks).

Two different varying photon patterns were used during the test. Each photon pattern was used for a defined period of time, after which the next photon pattern took over. A lifecycle of layer hens takes a much longer time compared to a broiler chicken lifecycle, thus the varying photon pattern was designed to take into account the shift in dominant wavelengths which occurs in natural sunlight throughout the day.

Photon pattern 1 (shown in Table 14) used a circadian cycle based lighting system starting at 6:00 in the morning and lasting until 22:00 in the evening. This experimental setup added extra energy in the cyan area of the spectrum compared to the test in example 10. Photon pattern 1 was used for 20 days.

TABLE 14

Photon pattern 1

Photon pattern 1

| | | | | | | | |
|---|---|---|---|---|---|---|---|
| Zone | 1 | | | | | | |
| Channel Amount | 7 | | | | | | |
| DMX Address | 1 | 2 | 3 | 4 | 5 | 7 | 8 |
| Channel Names | RED | GREEN | BLUE | WHITE | CYAN | UV_A | UV_C |
| Channel Colors | #FF0000 | #00FF00 | #0000FF | #FFDD00 | #00FFFF | #5E5EFF | #CACAFF |
| Dominant Wavelength | 627 nm | 530 nm | 470 nm | 3000K | 505 nm | 365 nm | 278 nm |

| Days | Timestamp | RED | GREEN | BLUE | WHITE | CYAN | UV_A | UV_C |
|---|---|---|---|---|---|---|---|---|
| 20 days | 00:00:01 | 0 | 0 | 1 | 0 | 0 | 0 | 0 |
| | 06:00:00 | 0 | | | 0 | | | |
| | 07:30:00 | 100 | | | 0 | | | |
| | 08:20:00 | | | | | 0 | | |
| | 09:00:00 | 225 | | 1 | 225 | | | |
| | 09:00:01 | | | | | | | |
| | 09:05:00 | | | | | | | |
| | 09:05:01 | | | | | | | |
| | 10:00:00 | | 0 | | | | | |
| | 10:00:01 | | | | | | | |
| | 10:05:00 | | | | | | | |
| | 10:05:01 | | | | | | | |
| | 11:30:00 | 255 | 255 | 255 | 255 | 255 | | |
| | 12:00:00 | | | | | | | |
| | 12:00:01 | | | | | | | |
| | 12:10:00 | | | | | | | |
| | 12:10:01 | | | | | | | |
| | 13:00:00 | | | | | | | |
| | 13:00:01 | | | | | | | |
| | 13:10:00 | | | | | | | |
| | 13:10:01 | | | | | | | |
| | 13:30:00 | 255 | 255 | 255 | 255 | 255 | | |
| | 14:00:00 | | | | | | | |
| | 14:00:01 | | | | | | | |
| | 14:10:00 | | | | | | | |

TABLE 14-continued

Photon pattern 1

| Timestamp | RED | GREEN | BLUE | WHITE | CYAN | UV_A | UV_C |
|---|---|---|---|---|---|---|---|
| 14:10:01 | | | | | | | |
| 15:00:00 | | 0 | | | | | |
| 15:00:01 | | | | | | | |
| 15:10:00 | | | | | | | |
| 15:10:01 | | | | | | | |
| 15:30:00 | | | 1 | | | | |
| 16:00:00 | | | | 0 | | | |
| 16:00:01 | | | | | | | |
| 16:05:00 | | | | | | | |
| 16:05:01 | | | | | | | |
| 18:00:00 | | | | 125 | | | |
| 18:00:01 | | | | | | | |
| 18:05:00 | | | | | | | |
| 18:05:01 | | | | | | | |
| 19:00:00 | 175 | | | | | | |
| 19:00:01 | | | | | | | |
| 19:05:00 | | | | | | | |
| 19:05:01 | | | | | | | |
| 20:00:00 | | | | | | | |
| 20:00:01 | | | | | | | |
| 22:00:00 | 0 | 0 | 1 | 0 | | | |
| 23:59:59 | 0 | 0 | 1 | 0 | 0 | 0 | 0 |

Photon pattern 2 (shown in Table 15) added UV-A and UV-C light to the spectrum. The UV-A emitters were activated from 9:00 to 20:00, while giving 4 short bursts (10 min) of UV-C light between 12:00 and 15:00. The UV-C light may additionally be useful in preventing infections by mite, lice etc. Photon pattern 2 was used for 498 days.

TABLE 15

Photon pattern 2

| Photon pattern 2 | | | | | | | | |
|---|---|---|---|---|---|---|---|---|
| Zone | 1 | | | | | | | |
| Channel Amount | 7 | | | | | | | |
| DMX Address | 1 | 2 | 3 | 4 | 5 | 7 | 8 | |
| Channel Names | RED | GREEN | BLUE | WHITE | CYAN | UV_A | UV_C | |
| Channel Colors | #FF0000 | #00FF00 | #0000FF | #FFDD00 | #00FFFF | #5E5EFF | #CACAFF | |
| Dominant Wavelength | 627 nm | 530 nm | 470 nm | 3000K | 505 nm | 365 nm | 278 nm | |

| Day | Timestamp | RED | GREEN | BLUE | WHITE | CYAN | UV_A | UV_C |
|---|---|---|---|---|---|---|---|---|
| 498 days | 00:00:01 | 0 | 0 | 1 | 0 | 0 | 0 | 0 |
| | 06:00:00 | 0 | | | 0 | | | |
| | 07:30:00 | 100 | | | 0 | | | |
| | 08:20:00 | | | | | 0 | | |
| | 09:00:00 | 225 | | 1 | 225 | | 0 | |
| | 09:00:01 | | | | | | 255 | |
| | 09:05:00 | | | | | | | |
| | 09:05:01 | | | | | | | |
| | 10:00:00 | | 0 | | | | | |
| | 10:00:01 | | | | | | | |
| | 10:05:00 | | | | | | | |
| | 10:05:01 | | | | | | | |
| | 11:30:00 | 255 | 255 | 255 | 255 | 255 | | |
| | 12:00:00 | | | | | | | 0 |
| | 12:00:01 | | | | | | | 255 |
| | 12:10:00 | | | | | | | 255 |
| | 12:10:01 | | | | | | | 0 |
| | 13:00:00 | | | | | | | 0 |
| | 13:00:01 | | | | | | | 255 |
| | 13:10:00 | | | | | | | 255 |
| | 13:10:01 | | | | | | | 0 |
| | 13:30:00 | 255 | 255 | 255 | 255 | 255 | | |
| | 14:00:00 | | | | | | | 0 |
| | 14:00:01 | | | | | | | 255 |
| | 14:10:00 | | | | | | | 255 |
| | 14:10:01 | | | | | | | 0 |
| | 15:00:00 | | 0 | | | | | 0 |
| | 15:00:01 | | | | | | | 255 |
| | 15:10:00 | | | | | | | 255 |
| | 15:10:01 | | | | | | | 0 |
| | 15:30:00 | | | 1 | | | | |
| | 16:00:00 | | | | | | 0 | |
| | 16:00:01 | | | | | | | |

TABLE 15-continued

| Photon pattern 2 | | | | | | | |
|---|---|---|---|---|---|---|---|
| 16:05:00 | | | | | | | |
| 16:05:01 | | | | | | | |
| 18:00:00 | | | | 125 | | | |
| 18:00:01 | | | | | | | |
| 18:05:00 | | | | | | | |
| 18:05:01 | | | | | | | |
| 19:00:00 | 175 | | | | | | |
| 19:00:01 | | | | | | | |
| 19:05:00 | | | | | | | |
| 19:05:01 | | | | | | | |
| 20:00:00 | | | | | 255 | | |
| 20:00:01 | | | | | 0 | | |
| 22:00:00 | 0 | 0 | 1 | 0 | | | |
| 23:59:59 | 0 | 0 | 1 | | 0 | 0 | 0 |

As shown in Table 15, there was a remarkable increase of vitamin D3 content (25% or more) as a result of the varying photo pattern.

TABLE 15

Resulting egg yolk Vit $D_3$ content based on the photon pattern and feed.

| | Photo pattern | Feed | Egg yolk Vit $D_3$ content (µg/100 g egg yolk) |
|---|---|---|---|
| Section 1 | UV spectrum | Normal feed | 5 |
| Section 2 | UV spectrum | Vit $D_3$ supplemented feed | 2.33 |
| Section 3 | Conventional lighting | Vit $D_3$ supplemented feed | 1.78 |
| Section 4 | Conventional lighting | Normal feed | 4 |

The two sections equipped with the LED lighting system according to the invention allowed the chickens to live 14 weeks longer, to 92 weeks.

Example

Spectra System

Figure 6:
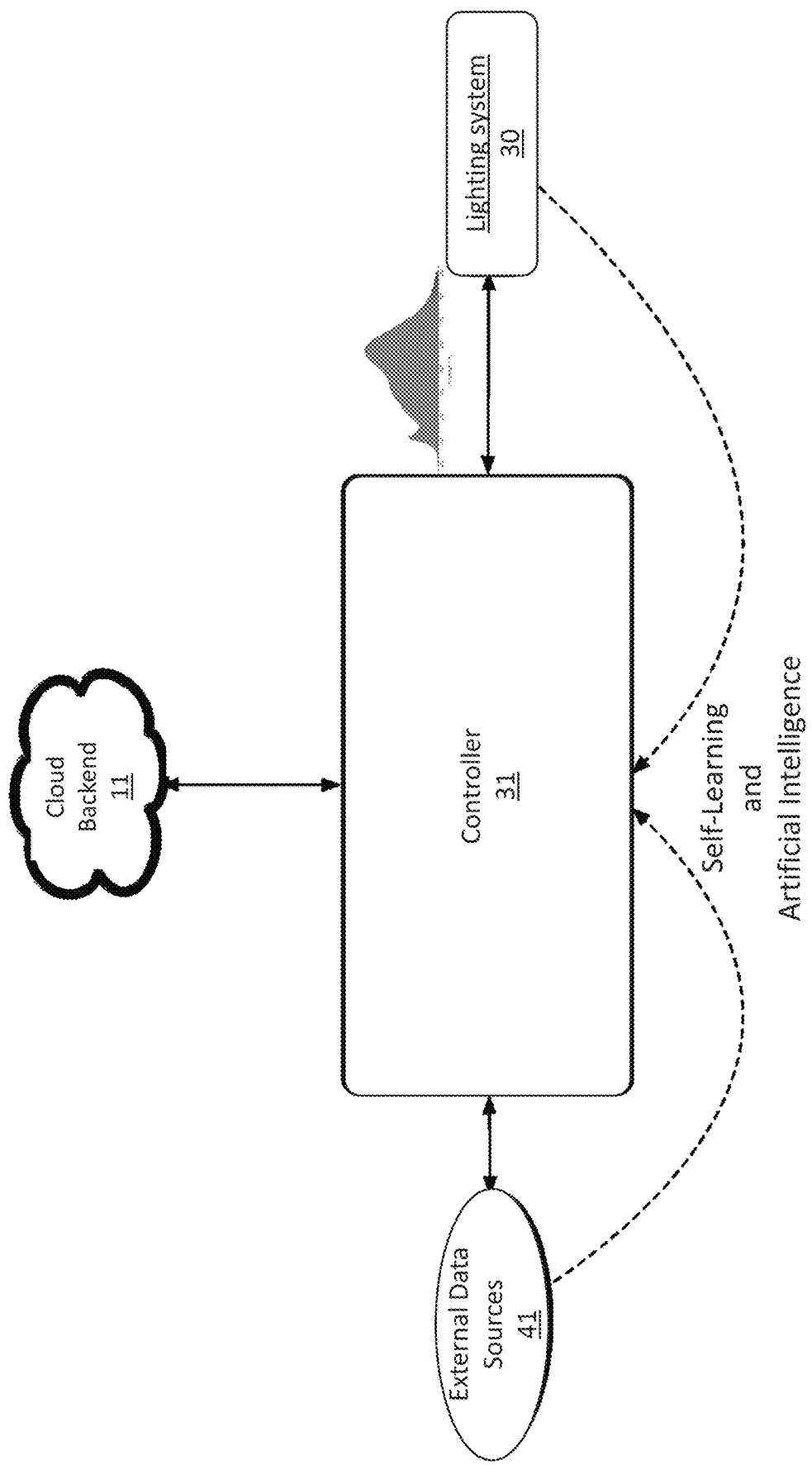
FIG. 6 shows a schematic view of a system according to the present disclosure.

With reference to FIG. 6, systems according to the present disclosure will now be described, hereinafter called the "Spectra system". The figure displays an overview of the Spectra system, comprising a hardware and a software application part. The system runs light algorithms that enable dynamic and variable lighting. Such light algorithms are called "Spectra Recipes" within the Spectra system.

Spectra System Overview

The following paragraph gives a global overview of the blocks used in such a system, after which each block is described in more detail. Spectra Recipes describe an ideal spectral composition of light, its variation over time and its bounds in space through abstract constraints, provoking a certain response in the living organisms affected by this light composition. Recipes are defined by non-volatile parameters through a custom devised file format (Spectra Recipe File, or SRF file) which state the recipe's core functionality and algorithmic response to input. Through volatile I/O from external data sources 41 the state and processing of the recipe can be altered to attain specific on-site needs and demands. The volatile I/O also provide a means of digesting, through self-learning, valuable feedback from the infrastructure on site in order to achieve better matching algorithmic output fitting the organisms needs in a more optimal way. The file format is human-readable, e.g. a textual representation of the algorithm and its parameters that can be distributed through data-exchange, for example through an internet connection towards the Spectra cloud backend 11.

Spectra recipes vary their output according to the current day and time. This time-induced variability changes the light output according to the needs of the organism. As such, cyclic repetitions of certain light patterns can be achieved, that can repeat once or multiple times per day. Each recipe is evaluated at least one time per second, meaning that its underlying algorithm calculates new output for the current state of all volatile and non-volatile parameters known at that time. The output is in the form of a Spectral Power Distribution (SPD), packed in a binary format. This SPD holds an abstract and ideal state of a light spectrum for a certain spatial location. It is fed into the next stage: a module mapping this ideal SPD to the actual light infrastructure.

This mapper module tries to match as close as possible the desired light spectrum to the current available light infrastructure. SPD's define a certain output power for a certain spectrum of wavelengths. SPD's are defined by their horizontal resolution (the granularity in which different wavelengths can be expressed) and the range in which wavelengths can be defined. This range doesn't necessarily have to coincide with the human visible spectrum, as other organisms can have a different biological perceptions of light. The lighting infrastructure can be composed of Spectra and non-Spectra lighting hardware. Spectra lighting hardware is fitted with bi-directional communication towards the Spectra controller 31 while their spectral characteristics of the inner (LED) components are generally matched to the Spectra Recipes typically used for certain organisms. However, a Spectra Controller 31 may be configured to also drive non-Spectra lights, such as more generic RGB LED-strip lights, through standard PWM-based dimming. In the latter case, the Spectra application may be configured to be aware of the spectral characteristics of this generic lighting.

Site specific information is stored inside a local database, comprising the current state of the system, information about the organism type and age present in the infrastructure and information about its dimensions and metrics. The database also contains a provisioning profile and unique key (UUID) for that system for safe and encrypted communication to the Spectra cloud backend 11. The cloud backend 11 provides an opportunity to control in a global way multiple Spectra systems, deploy and activate SRF files and ascertain current state.

SRF files are principally defined through research and test setups distributed over different infrastructures and organisms. These setups provide a base SPD definition, and are the base composition of lights for which results can then be measured. Through a self-learning process and connection to external data sources 41, the controller 31 can gather metrics about the spectral efficiency and record the response of the organism related to the desired response. The infrastructure can be fitted with I/O hardware, sensors and sound/imaging devices that provide better and more meaningful input to this end. Alterations can be stored locally and taken in account during following iterations of the algorithm, but can also be communicated back to the Spectra Cloud backend 11 such that the altered and improved SRF files can be deployed on other sites.

It must be noted that the terms "input system" and "external data source" are used interchangeably under appropriate conditions where the external data source is used as an input system.

Spectra Recipe Non-Volatile File Format (SRF)

This Spectra Recipe File Format (SRF) proposes a digital way of defining light algorithms.

The format defines light that
has a specific spectral composition fitting the needs of the organism affected by it
is dynamic and variable over time
has spatial constraints
is variable over the lifecycle of the organism A light algorithm generates an ideal SPD for a current state of parameters and volatile I/O. These parameters define the type and age of the organism that is affected by the light. Moreover, a desired and ideal SPD is defined for certain time key frames for a certain spatial constraint.

This spatial constraint defines the reference distance the light should reflect on the organism or surface as defined in the recipe. This reference distance is scaled and adjusted in the mapper module according to on-site values, which differs from site to site. The controller 31 interpolates between key frames and generates at least one time per second an intermediary SPD that reflects an ideal light composition for that time point and spatial constraint. During the interpolation, a certain slope can be taken into account in order to avoid fast jumps in chromaticity or luminance of the lights.

By alternating/interpolating between certain blocks of constant spectral output and varying the length of each block, a spectral composition can be made that runs dynamically over time (as analogous to a musical composition). This also enables cyclic repetitions of spectral composed light once or multiple time per day.

Volatile I/O from External Data Sources

The Spectra hardware platform is equipped to accept input from different external sources 41, such as:
  Generic I/O: e.g. digital 5V input trigger
  Date/Time: can be originating from internal source, such as an RTC module, but can also be synchronized with online source, through for example NTP
  Sound/Image: audio capture or imaging devices may be present in the scene enabling to adjust the recipe according to certain stimuli that may signal distress, emergency, . . .
  0/10V input: to regulate global brightness levels of light output. The Spectra hardware board has multiple inputs of this type, enabling individual brightness control per zone
  Data from other external sources (stable management computers, technical infrastructure management systems and other data systems) through their respective APIs Mapper Module This component takes care of mapping the generated SPD, or spectral composition, to the actual light infrastructure present on site. When an SPD is given for outputting photonic power in the short wavelength range (indigo-blue colors), the mapper tries to match this to the light infrastructure that is defined for the specific site. The mapper tries to fit the desired spectral output as best as possible. For example: a dimmed white light can be produced by equally dimming PWM levels of an RGB LED-strip but also by driving a Spectra type lamp equipped with only white LEDs. Lamp types (with different spectral compositions) can be configured on the fly and synchronized with the Spectra cloud backend 11.

The mapper takes in account spatial constraints such that recipes can scale their output to compensate for larger or smaller spaces equipped with lighting infrastructure. As such, a Spectra Recipe describes an ideal spectral wavelength composition where the power is relative to an ideal spatial situation. The Spectra software mapper then translates this ideal situation to the actual on-site spatial dimensions.

Connection to Site-Specific Infrastructure

Spectra lamps use a data protocol to enable bi-directional communication from and towards the Spectra controller 31. This protocol is proprietary and handles discovery of lamps connected to the controller 31 (with their spectral characteristics), light output control and error handling. Lamps can be configured into groups, resulting in equal color and equal intensity light in different zones.

Local Database

The local database contains site specific information such as infrastructure spatial metrics (for example a 3D model), the site's organism type and age, which I/O can be used or is present on site and the specific zone layout. It also contains a footprint of the current state of the controller 31 and a provisioning profile to enable cloud communication. In case of errors and power issues this database enables the application to continue the previous operation state, minimally affecting the organism.

Cloud Backend

The Spectra cloud backend 11 provides a means to control Spectra systems through a web interface in a de-localized way. Each system is provisioned to alert its state to this backend and is able to receive command this way. The backend furthermore serves as a sink for error reports and on-site defined lamp types. When on-site recipe feedback is generated, the backend can serve as a gathering point to enable data analysis and improved recipe generation.

Self-Learning Feedback Loop

A Spectra Controller 31 is able to parse feedback on how the affected organism behaves for the current spectral composition of light and how this relates to the ideal target state that was preset to achieve. This allows the system to perform self-learning and fine-tune its performance to the on-site infrastructure and overall parameters, while also providing feedback about the overall efficiency of the Spectra Recipe. The connection with the Spectra backend provides a means to distribute this feedback enabling integration on other sites.

Feedback can include distress state of the organism, growth or the absence of it, auditive signals that signal certain behavior and others. Measuring such signals can serve as input to correct and improve recipes, and provide valuable data sets for further offline or remote data analysis. Feedback data can also originate from stable management systems and other external data sources 41.

Initial SRF Definition Through Research

Several test sites have been equipped with Spectra hardware and software. This generates data sets that can be evaluated to form initial Spectra recipes. As outlined in the previous section, a Spectra system can benefit from utilizing constant monitoring and feedback apparatus to improve recipes through data analysis.

Worked Example

One Spectra test site comprises of a chicken layer stable where six zones of chickens reside on the ground floor. A Spectra system is installed to control all six zones. Each zone has Spectra bi-color lamps, that can operate in short wavelength mode (through blue color LEDs) or in overall white mode (through white LEDs). Each channel is dimmable through Spectra protocol commands. The lights are mounted on top of the region where there is an automatic transporter band for the chickens eggs when they are laid each morning, which accounts for only a small part of their total space.

A common issue with chicken layer stables are the so-called 'ground eggs'. These are eggs that aren't produced in the space with the transporter band but are produced in the other part of their space, on the ground, causing labor-intensive work to collect each egg and put in on the transporter band. Spectra research has shown that producing blue light in the morning significantly lowers the need for the chickens to produce 'ground eggs' and produce their eggs in the transporter band zone. In the afternoon, the lights can switch back to white light.

A Spectra system and recipe linked to the above situation is shown in FIG. 6. Here, a recipe will contain time points where the light will toggle between a dominantly blue spectrum and an overall white spectrum.

The invention claimed is:

1. A non-transient storage medium containing an algorithm in a format executable by a control system of a multicolor LED lighting system,
    wherein, the algorithm controls the multicolor LED lighting system to generate a photon pattern,
    wherein the photon pattern induces a desired response in an organism, the algorithm comprising a set of instructions that causes the control system to operate a plurality of LEDs of the multicolor LED lighting system to emit at least one predetermined varying photon pattern,
    wherein the set of instructions defines at least the following group of parameters for each of the at least one predetermined varying photon pattern: a target location, an intensity, a duty cycle and a wavelength band, and a variation of at least one of the parameters over time, and
    wherein the set of instructions is provided to cause the control system to operate the plurality of LEDs of the multicolor LED lighting system such that for at least 50% of the plurality of LEDs comprised in the multicolor LED lighting system, a change of the intensity of a LED over a time period of at least 1 ms is lower than 90% of the maximum intensity of the LED,
    wherein the control system generates the set of instructions based on an input data and a stored input data,
    wherein the algorithm further comprises an instruction for obtaining the input data from one or more sensors,
    wherein the input data is further classified based on a learned classification model to generate a classification attribute of the input data, and
    wherein the set of instructions is further based on the classification attribute, further
    wherein the set of instructions further includes a response feedback mechanism, the response feedback mechanism comprising the steps of:
        receiving the input data, wherein the input data includes a status of inducing a current desired response,
        optionally altering a sequence of photon patterns associated with desired responses,
        optionally defining new subgroups, and
        adapting or maintaining the set of instructions based on the input data;
    wherein a first subgroup of LEDs and a second subgroup of different LEDs from among the plurality of LEDs, in the multicolor LED lighting system, are configured to emit the at least one predetermined varying photon pattern,
    wherein the set of instructions for the first subgroup of LEDs and the second subgroup of LEDs differ in at least one of the following parameters: intensity, duty cycle, wavelength band or the variation of the parameters over time,
    wherein the first subgroup of LEDs emits photons that are unattractive to the organism and the second subgroup of LEDs emits photons that are attractive to the organism.

2. The non-transient storage medium according to claim 1, wherein the set of instructions further defines target subgroups of LEDs within the multicolor LED lighting system for emission of the at least one predetermined varying photon pattern.

3. The non-transient storage medium according to claim 1, wherein the set of instructions further causes the control system to operate LEDs of the multicolor LED lighting system to emit a sequence of predetermined varying photon patterns to induce a sequence of desired responses in one or more organisms.

4. The non-transient storage medium according to claim 1, wherein the set of instructions further includes a fail-safe mechanism, provided for detecting and preventing the execution of a forbidden or an undesirable instruction contained in the algorithm.

5. The non-transient storage medium according to claim 1, wherein the algorithm is in a human-readable format.

6. The non-transient storage medium according to claim 1, wherein the input data regarding the status of inducing the current desired response is output data received from a self-learning image recognition system and/or a self-learning sound recognition system.

7. The non-transient storage medium according to claim 6, wherein the algorithm further comprises an instruction for storing the input data and the corresponding adapted set of instructions or maintained set of instructions in one or more databases.

8. The non-transient storage medium according to claim 7, wherein the step of adapting or maintaining the set of instructions comprises a comparison of the input data with the stored input data and determining whether to adapt or maintain the instructions based on the comparison.

9. The non-transient storage medium according to claim 1, wherein the organism is an animal, and wherein the algorithm further comprises an instruction for obtaining the input data from one or more sensors.

10. The non-transient storage medium according to claim 9, wherein the desired response comprises one or more of the group consisting of: increasing egg production; increasing the average lifespan of poultry; improving animal welfare; improvement or prophylaxis of footpad dermatitis; decreasing a footpad dermatitis score; decreasing a hock burn score; improving activity; increasing egg vitamin $D_3$ content; decreasing parasite infection; decreasing ground eggs; increasing egg shell thickness; eating; drinking; and/or moving to or away from a predetermined area.

11. The non-transient storage medium according to claim 9, wherein the desired response comprises increasing egg production and/or decreasing ground eggs and wherein the at least one predetermined varying photon pattern is such that within a timeframe of 3 hours, the photon pattern comprises predominantly blue light, for at least 5 minutes.

12. The non-transient storage medium according to claim 9, wherein the desired response comprises improving activity, improvement or prophylaxis of footpad dermatitis, and/or decreasing a footpad dermatitis score; decreasing a hock burn score; and wherein the at least one predetermined varying photon pattern is such that within a timeframe of 3 hours, a same area is dominated by blue light for at least 1 minute, and by red light for at least 1 minute.

13. The non-transient storage medium according to claim 9, wherein the desired response comprises increasing egg vitamin $D_3$ content and wherein the at least one predetermined varying photon pattern is such that within a timeframe of 24 hours, at least one burst of UV-C light of at least 1 minute is emitted.

14. The non-transient storage medium according to claim 9, wherein the desired response comprises increasing egg vitamin $D_3$ content and wherein the at least one predetermined varying photon pattern is such that within a timeframe of 24 hours, UV-A light of 355-375 nm of is emitted for at least one or more hours.

15. A multicolor LED lighting system comprising a plurality of LEDs and a control system configured for operating the plurality of LEDs, the control system comprising at least one algorithm according to claim 1, wherein the control system comprising a mapping module for mapping the at least one algorithm on the plurality of LEDs that are present in the multicolor LED lighting system.

16. The multicolor LED lighting system according to claim 15, wherein the control system comprises at least one input for receiving feedback signals from a feedback mechanism and wherein the control system is adapted for evaluating the feedback signals and adapting its operation of the plurality of LEDs based on the evaluation.

17. The multicolor LED lighting system according to claim 15, further comprising a computer system being provided with one or more image and/or sound recognition software applications.

18. An animal facility comprising a multicolor LED lighting system according to claim 15.

* * * * *